United States Patent [19]

Oguri et al.

[11] Patent Number: 4,613,613
[45] Date of Patent: Sep. 23, 1986

[54] γ-BUTYROLACTONE DERIVATIVES, PROCESS FOR PREPARING THE SAME AND IMMUNOMODULATING COMPOSITIONS CONTAINING THE SAME AS ACTIVE INGREDIENTS

[75] Inventors: Tomei Oguri; Yasuhiro Morinaka; Shuichiro Kadowaki, all of Ami, Japan

[73] Assignee: Mitsubishi Yuka Pharmaceutical Co., Ltd., Tokyo, Japan

[21] Appl. No.: 647,979

[22] Filed: Sep. 6, 1984

[30] Foreign Application Priority Data

Sep. 13, 1983 [JP] Japan .................. 58-167521

[51] Int. Cl.$^4$ ............ A61K 31/365; A61K 31/34; C07D 307/10; C07D 307/26
[52] U.S. Cl. ................. 514/461; 514/462; 514/471; 549/323; 549/330
[58] Field of Search ............ 549/313, 315, 323; 514/461, 473, 462, 471

[56] References Cited

U.S. PATENT DOCUMENTS 3,328,415  6/1967  Surrey et al. .................. 549/313

FOREIGN PATENT DOCUMENTS

| 1920176 | 10/1970 | Fed. Rep. of Germany | 549/313 |
| 0416331 | 4/1966 | Japan | 549/323 |
| 0183778 | 11/1982 | Japan | 549/313 |
| 0008004 | 1/1983 | Japan | 549/313 |
| 0079989 | 5/1983 | Japan | 549/313 |
| 1075456 | 7/1967 | United Kingdom | 549/313 |
| 2114571 | 8/1983 | United Kingdom | 549/313 |

OTHER PUBLICATIONS

Corbit et al, CA 94 p. 635 #120815g 1981, Allegerics & Methylene-γ-Lactones.
Fuchs, "Some 2- or 3-Mercapto Substituted γ-Lactones Ark. Kemi., 26(10), pp. 111–116 (compounds (A) & (B) are disclosed).
Martin, "A New Approach to the Synthesis of α-Alkylidene-γ-Butyrolactones and Δ$^{\alpha,\beta}$-Butenolides" Tetrahedron Letters, 1976(49), pp. 4459–4462 (compound (C) disclosed).
Ronald, "A New Method for Methyleneation of Butyrolactones" Tetrahedron Letters, 1973(39), pp. 3831–3834 (compound (D) disclosed).
Greico, "Blocking and Deblocking of α-Methylene-γ-Butyrolactones" J. Org. Chem., 40(8), 1975, pp. 1181–1183 (compd. (E) disclosed).
Cassidy, "Potential Antitumor Agents, Synthesis, Reactivity, and Cytotoxicity of α-Methylene Carbonyl Compounds" J. Med. Chem., 21(8), 1978, pp. 815–819 (compds. (F) & (G) disclosed.
Klotz, "Sulfur-Containing Derivatives of Proteins" Biochim. Biophys. Acta., 100(1), (1965), pp. 104–110 (compd. (H) disclosed).

Primary Examiner—Albert T. Meyers
Assistant Examiner—D. L. Dinner
Attorney, Agent, or Firm—Frishauf, Holtz, Goodman & Woodward

[57] ABSTRACT

A γ-butyrolactone derivative represented by the following formula:

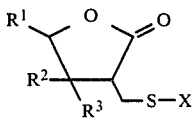

wherein $R^1$ represents a hydrogen atom, a straight or branched alkyl group having 1–8 carbon atoms, a phenyl group; $R^2$ and $R^3$ may be the same or different and each represents a hydrogen atom, a straight or branched alkyl group having 1–8 carbon atoms, a cycloalkyl group having 3–10 carbon atoms, a benzyl group, a phenyl group, a phenyl group substituted with a substituent selected from the group consisting of a halogen atom, an alkoxy group, a nitro group, an amino group, an alkyl group having 1–4 carbon atoms, a nitrile group and an alkoxycarbonyl group; $R^2$ and $R^3$ may be linked to form an alkylene group having 4–6 carbon atoms; X represents a hydrogen atom, a straight or branched alkyl group having 1–8 carbon atoms, a cycloalkyl group having 3–10 carbon atoms, a benzyl group or a substituent represented by the formula

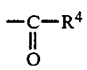

(wherein $R^4$ represents a straight or branched alkyl group having 1–8 carbon atoms, a cycloalkyl group having 3–10 carbon atoms, a benzyl group, a phenyl group or a phenyl group substituted with a substituent selected from the group consisting of a halogen atom, an alkoxy group, a nitro group, an alkylthio group, a nitrile group, an alkoxycarbonyl group and an alkyl group having 1–4 carbon atoms) or a salt thereof. The invention also provides an immunomodulating composition wherein the aforedescribed compound is the active component.

8 Claims, No Drawings

γ-BUTYROLACTONE DERIVATIVES, PROCESS FOR PREPARING THE SAME AND IMMUNOMODULATING COMPOSITIONS CONTAINING THE SAME AS ACTIVE INGREDIENTS

BACKGROUND OF THE INVENTION

This invention relates to new γ-butyrolactone derivatives, namely α-mercaptomethyl-γ-butyrolactone derivatives, to process for preparing the same and to immunomodulating compositions containing the same as an active ingredient.

As a therapeutic agent against rheumatoid arthritis, one of representative autoimmune diseases, there are roughly classified into an anti-inflammatory agent and an immunomodulating agent. The former is a palliative agent and can not be an agent for complete recovery. On the other hand, the latter has been given attention for last several years as a therapeutic agent based on etiology. As such an immunomodulating agent, there have been proposed a gold preparation, D-penicillamine, levamisole, N-(2-carboxyphenyl)-4-chloroanthranilic acid disodium salt (CCA) and the like. However, such drugs show a strong toxicity to a living body and hence it is the present status that a satisfactory therapeutic agent has not yet been developed. Moreover, as sulfur-containing γ-butyrolactone analogous compounds, there have been reported those compounds represented by the formulae

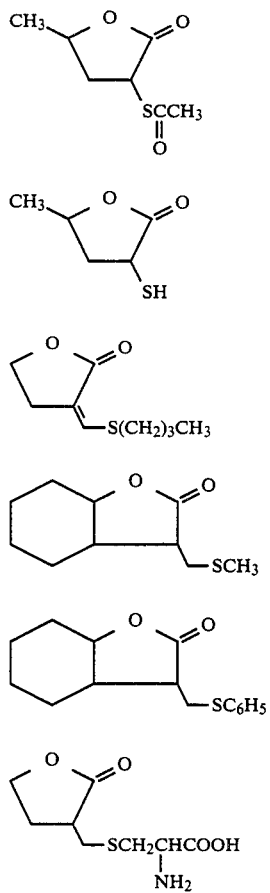

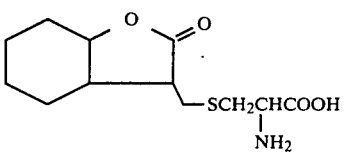

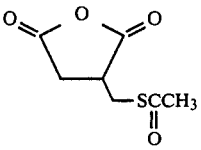

and the like in literatures [Ark. Kemi., 26 (10), 111 (1966); Tetrahedron Letters, 1976 (49), 4459; Tetrahedron Letters, 1973 (39), 3831; J. Org. Chem., 40 (8), 1181 (1975); J. Med. Chem., 21 (8), 815 (1978); Biochim. Biophys. Acta., 100 (1), 104 (1965)]; However, they did not at all disclose an immunomodulating activity.

SUMMARY OF THE INVENTION

The present inventors have found that novel α-mercaptomethyl-γ-butyrolactone derivatives exert a remarkable antibody formation potentiating activity (an immunopotentiating activity) in animals and further shows an excellent effect against adjuvant arthritis, a pathological model of rheumatoid arthritis which is a representative autoimmune disease. They also developed a novel process for preparing the same and thus completed the present invention.

This invention provides γ-butyrolactone derivatives of the general formula (I):

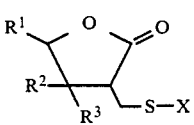

wherein $R^1$ represents a hydrogen atom, a straight or branched alkyl group having 1–8 carbon atoms, a substituted or unsubstituted cycloalkyl group having 3–10 carbon atoms or a substituted or unsubstituted phenyl group; $R^2$ and $R^3$ may be the same or different and each represents a hydrogen atom, a straight or branched alkyl group having 1–8 carbon atoms, a substituted or unsubstituted cycloalkyl group having 3–10 carbon atoms, a substituted or unsubstituted phenyl group or a substituted or unsubstituted aralkyl group having 7–12 carbon atoms or a mutually linked alkylene group having 4–6 carbon atoms; X represents a hydrogen atom, a straight or branched alkyl group having 1–8 carbon atoms, a substituted or unsubstituted cycloalkyl group having 3–10 carbon atoms, a substituted or unsubstituted aralkyl group having 7–12 carbon atoms or a substituent represented by the formula $$-\underset{\underset{O}{\|}}{C}-R^4$$

(wherein $R^4$ represents a straight or branched alkyl group having 1–8 carbon atoms, a substituted or unsubstituted cycloalkyl group having 3–10 carbon atoms, a substituted or unsubstituted phenyl group or a substituted or unsubstituted aralkyl group having 7-12 carbon atoms)] or a salt thereof.

DESCRIPTION OF THE PREFERRED EMBODIMENTS

In the above formula (I), as the straight or branched alkyl group having 1-8 carbon atoms, there may be mentioned a methyl group, an ethyl group, a n-propyl group, an isopropyl group, a n-butyl group, a sec-butyl group, an isobutyl group, a tert-butyl group, a n-amyl group(a n-pentyl group), an isoamyl group(an isopentyl group), a sec-amyl group, an active amyl group(a 2-methylbutyl group), a tert-amyl group, a neopentyl group, a 1-ethylpropyl group, a 1,2-dimethylpropyl group, a n-hexyl group, a n-heptyl group, a n-octyl group and the like. As the substituted or unsubstituted cycloalkyl group having 3-10 carbon atoms, there may be mentioned a cyclopropyl group, a 2-methylcyclopropyl group, a 2,2-dimethylcyclopropyl group, a cyclobutyl group, a 2-methylcyclobutyl group, a 3-methylcyclobutyl group, a cyclopentyl group, a 2-methylcyclopentyl group, a 3-methylcyclopentyl group, a 2,2-dimethylcyclopentyl group, a cyclohexyl group, a 4-methylcyclohexyl group, a 3-methylcyclohexyl group, a 2-methylcyclohexyl group, a 4-ethylcyclohexyl group, a 3-ethylcyclohexyl group, a 2-ethylcyclohexyl group, a 4-tert-butylcyclohexyl group, a 4-methoxycyclohexyl group, a 4-hydroxycyclohexyl group, a 4-aminocyclohexyl group, a 4-ethoxycarbonylcyclohexyl group, a 4-carboxycyclohexyl group and the like. As the substituent for a phenyl group, there may be mentioned a straight or branched alkyl group having 1-5 carbon atoms such as a methyl group, an ethyl group, a n-propyl group, an isopropyl group, a n-butyl group, a tert-butyl group, a n-amyl group, an isoamyl group, a neopentyl group; a straight or branched alkoxy group having 1-5 carbon atoms such as a methoxy group, an ethoxy group, a n-propoxy group, an isopropoxy group, a n-butoxy group, a tert-butoxy group, a n-amyloxy group, a neopentyloxy group; a straight or branched alkoxycarbonyl group having 2-6 carbon atoms such as a methoxycarbonyl group, an ethoxycarbonyl group, a n-propoxycarbonyl group; a straight or branched alkylthio group having 1-5 carbon atoms such as a methylthio group, an ethylthio group, a n-propylthio group, an isopropylthio group; a straight or branched alkylsulfonyl group having 1-5 carbon atoms such as a methylsulfonyl group, an ethylsulfonyl group, a n-propyl sulfonyl group, an isopropylsulfonyl group; a halogen atom such as a fluorine atom, a chlorine atom, a bromine atom, an iodine atom; a substituted or unsubstituted amino group such as an amino group, a monomethylamino group, a monoethylamino group, a dimethylamino group, a diethylamino group, a methylethylamino group, a phenyl amino group, a benzylamino group; a cyano group, a nitro group, a hydroxy group, a carboxyl group and the like, a phenyl group being optionally substituted with 1-3 of said substituents. As the aralkyl group having 7-12 carbon atoms, there may be mentioned a benzyl group, a phenethyl group, a phenylpropyl group, a β-methylphenethyl group, an α-methylphenethyl group and the like, an aralkyl group being optionally substituted with 1-3 of the substituents mentioned above with regard to a phenyl group.

In the compound of the above formula (I), $R^1$ is preferably a hydrogen atom, a straight alkyl group having 1-4 carbon atoms or a phenyl group, one of $R^2$ and $R^3$ is preferably a hydrogen atom and the other is preferably a hydrogen atom, a substituted or unsubstituted phenyl group, a benzyl group or a cyclohexyl group or both are preferably jointed to form an alkylene group having 4 or 5 carbon atoms, X is preferably a hydrogen atom, a straight alkyl group having 1-4 carbon atoms, a cyclohexyl group, a benzyl group, a benzylcarbonyl group, a straight or branched alkanoyl group having 2-9 carbon atoms or a substituted or unsubstituted benzoyl group.

Further, in the compound of the above formula (I), $R^1$ is more preferably a hydrogen atom or a phenyl group, one of $R^2$ and $R^3$ is more preferably a hydrogen atom and the other is a hydrogen atom, a substituted or unsubstituted phenyl group or cyclohexyl group, X is more preferably a hydrogen atom, a straight alkyl group having 1-4 carbon atoms, a cyclohexyl group, a benzyl group, a benzylcarbonyl group, a straight or branched alkanoyl group having 2-7 carbon atoms or a substituted or unsubstituted benzoyl group.

Moreover, the compounds of the above formula (I) wherein $R^1$ is a hydrogen atom, one of $R^2$ and $R^3$ is a hydrogen atom and the other is substituted or unsubstituted phenyl group, X is a straight or branched alkanoyl group having 2-7 carbon atoms or a substituted or unsubstituted benzoyl group are most preferable.

The present γ-butyrolactone derivatives represented by the above formula (I) may be prepared according to the process which comprises reacting a compound represented by the formula

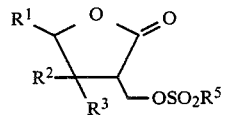

wherein $R^1$, $R^2$ and $R^3$ have the same meanings as defined above, and $R^5$ represents a straight or branched alkyl group having 1-5 carbon atoms or an aryl group having 6-10 carbon atoms with a compound represented by the formula

wherein X has the same meaning as defined above and $M^1$ represents a hydrogen atom or an alkali metal atom to form a compound represented by the formula (I);

or reacting a compound represented by the formula

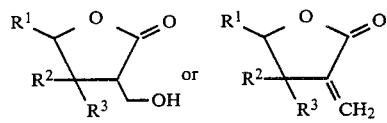

wherein $R^1$, $R^2$ and $R^3$ have the same meanings as defined above, with a compound represented by the formula

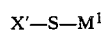

wherein X' represents X except for a hydrogen atom, and $M^1$ has the same meaning as defined above, provided that the reaction is carried out in the presence of a dehydrogenation agent and a deoxidation agent in cases where the starting γ-butyrolactone derivative is an α-hydroxymethyl derivative, to form a compound represented by the formula

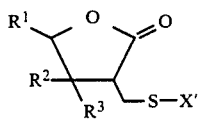

wherein $R^1$, $R^2$, $R^3$, $R^4$ and $X'$ have the same meanings as defined above;
or reacting a compound represented by the formula

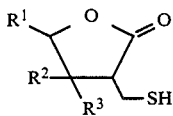

wherein $R^1$, $R^2$ and $R^3$ have the same meanings as defined above,
with an acylating agent selected from the group consisting of

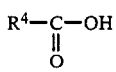

(in which $R^4$ has the same meaning as defined above) and its functionally modified derivatives or an alkylating agent represented by the formula $R^6X^1$ wherein $R^6$ represents a straight or branched alkyl group having 1-8 carbon atoms, a substituted or unsubstituted cycloalkyl group having 3-10 carbon atoms or a substituted or unsubstituted aralkyl group, and $X^1$ represents a halogen atom or a sulfonic acid ester residue,
to form a compound represented by the formula

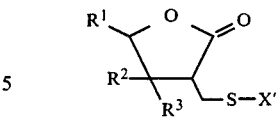

wherein $R^1$, $R^2$, $R^3$ and $X'$ have the same meanings as defined above.

The synthetic routes [A-1]–[A-9] are as follows.

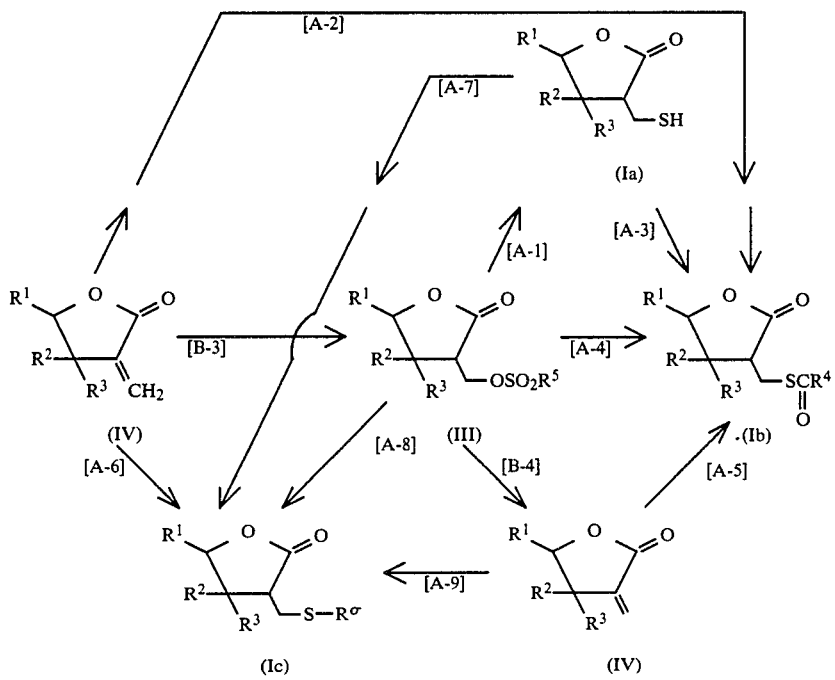

In the Synthetic routes, $R^1$, $R^2$, $R^3$ and $R^4$ are as defined above, $R^5$ represents a straight or branched alkyl group having 1-5 carbon atoms or an aryl group having 6-10 carbon atoms and $R^6$ represents a straight or branched alkyl group having 1-8 carbon atoms, a substituted or unsubstituted cycloalkyl group having 3-10 carbon atoms or a substituted or unsubstituted aralkyl group having 7-12 carbon atoms.

The compound (Ia) of the formula (I) wherein X is a hydrogen atom may be prepared from an α-sulfonyloxymethyl-γ-butyrolactone (III) (Synthetic route [A-1]). The compound (Ib) wherein X is a group of the formula

(in which $R^4$ is as defined above) may be prepared from an α-hydroxymethyl-γ-butyrolactone (II), an α-mercaptomethyl-γ-butyrolactone (Ia), an α-sulfonyloxymethyl-γ-butyrolactone (III) or an α-methylene-γ-butyrolactone (IV) (Synthetic routes [A-2]–[A-5]). The compound (Ic) wherein X is the said $R^6$ may be also prepared from similar staring material in the compound (Ib) (Synthetic routes [A-6]–[A-9]).

The above-mentioned Synthetic routes [A-1]–[A-9] will be illustrated in detail hereinbelow.

In Step [A-1], the desired product (Ia) may be prepared by subjecting the compound (III) to replacement reaction in a suitable solvent with potassium hydrosulfide or sodium hydrosulfide or with a gaseous hydrogen sulfide in the presence of a base. As the solvent, there may be employed an alcohol such as methanol, ethanol, n-propanol and the like; an ether such as ethyl ether, dioxane, tetrahydrofuran and the like; an aprotic polar solvent such as dimethylformamide, dimethylacetamide, hexamethylphosphoramide, dimethyl sulfoxide and the like.

Reaction temperature is $-20°$-$150°$ C. and, particularly, $-5$ -$50°$ C. is preferable. Reaction period of time is 5 minutes to 72 hours, preperably 1–48 hours. Pressure is 1–10 atmospheric pressure, preferably 1–3 atmospheric pressure. Also, it is preferable for smooth reaction to add acetic acid, propionic acid and so on.

Sodium hydrosulfide or potassium hydrosulfide is used at 0.8–4 times moles, preferably 1–3 times moles, to the starting material (III). After completion of the reaction, the compound (Ia) can be obtained by extraction with a conventional extraction solvent, removal of the solvent with distillation and, if necessary, purification with chromatography or recrystallization.

In Step [A-2], the desired product (Ib) may be obtained by treatment of the compund (II) with a thiolcarboxylic acid or a salt thereof represented by the formula

(wherein $R^4$ is as defined above, $M^1$ is a hydrogen atom or an alkali metal such as lithium, sodium, potassium atom) in the presence of a dehydrogenation agent and a deoxidation agent in a suitable solvent. As the solvent, there may be employed an ether such as diethyl ether, tetrahydrofuran, dioxane and the like; an alkyl halide such as chloroform, dichloromethane, trichlene and the like; an aromatic hydrocarbon such as benzene, toluene, xylene and the like. As the dehydrogenation agent, there may be employed a diester of an azodicarboxylic acid such as diethyl azodicarboxylate, diisopropyl azodicarboxylate and the like. Its amount to be used is 0.8–4 times moles, preferably 1–2 times moles, to the starting material (II). As the deoxidation agent, there may be employed a phosphine such as triphenyl phosphine, tri-n-butyl phosphine, triethyl phosphine and the like. Its amount to be used is 0.8–4 times moles, preparably 1–3 times moles, to the starting material (II). Reaction temperature is $-20°$-$120°$ C., particularly, $-5°$-$50°$ C. being preferable. Reaction period of time is 10 minutes to 48 hours and 30 minutes to 10 hours are particularly preferable. Reaction pressure is 1–10 atmospheric pressures, preferably 1–3 atmospheric pressures. The thiolcarboxylic acid or salt thereof is used at 0.8–4 times moles, preferably 1–3 times moles, to the starting material (II). After completion of the reaction, the reaction mixture is, if necessary, diluted with a suitable solvent, washed with water and then the solvent is distilled off. Purification by a conventional method such as recrystallization or chromatography gives the compound (Ib).

In Step [A-3], the desired product (Ib) may be obtained by acylation of the compound (Ia) with an acid anhydride represented by the formula

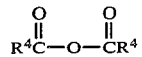

(wherein $R^4$ is as defined above) or an acid halide represented by the formula

(wherein $R^4$ is as defined above and Hal represents a halogen atom such as a chlorine atom, a bromine atom and the like) in the presence of a base in a suitable solvent (Method A), or by treatment of the compound (Ia) with a free carboxylic acid represented by the formula

wherein $R^4$ is as defined above) in the presence of a dehydration condensation agent and a base in a suitable solvent (Method B).

In Method A, as the solvent, there may be employed an aromatic hydrocarbon such as toluene, benzene, xylene and the like; an ether such as diethyl ether, tetrahydrofuran, dioxane and the like; an alkyl halide such as chloroform, dichloromethane, Tri-Clene(trichloroethylene) and the like; a ketone such as acetone, methyl ethyl ketone and the like; and so on. As the base, there may be employed a tertiary amine such as triethylamine, trimethylamine, N,N-dimethylaniline, pyridine, lutidine and the like; an alkali metal hydroxide such as sodium hydroxide, potassium hydroxide, lithium hydroxide and the like; an alkali metal carbonate such as sodium carbonate, potassium carbonate, sodium hydrogencarbonate, lithium carbonate and the like; and so on. Its amount to be used is 0.8–4 times moles, preferably 1–2 times moles, to the acid anhydride or acid halide. Reaction temperature is $-20°$-$150°$ C., preferably $-5°$-$50°$ C. Reaction period of time is 10 minutes to 72 hours, preferably 1–10 hours. Reaction pressure is 1–10 atmospheric pressure, preferably 1–3 atmospheric pressure. The acid anhydride or acid halide is used at 0.8–4 times moles, preferably 1–3 times moles, to the compound (Ia). After completion of the reaction, the reaction mixture is, if necessary, diluted with an extraction solvent, washed with water and then the solvent is distilled off. Purification by a conventional method such as recrystallization or chromatography gives the desired product (Ib).

In Method B, as the solvent, there may be used an alkyl halide such as chloroform, dichloromethane, Tri-Clene and the like; an aromatic hydrocarbon such as toluene, benzene, xylene and the like; an aprotic polar solvent such as dimethylformamide, phosphoric hexamethyltriamide, dimethylacetamide and the like; an ether such as diethylether, tetrahydrofuran, dioxane and the like; and so on. As the dehydration condensation agent, there may be used dicyclohexylcarbodiimide, diphenylphosphoryl azide, diethylphosphoryl cyanide and the like and its amount to be used is 0.8–4 times moles, preferably 1–3 times moles, to the starting material (Ia). As the base, there may be used a tertiary amine such as triethylamine, trimethylamine, pyridine, lutidine, dimethylaniline and the like. Its amount to be used is 0.8–4 times moles, preferably 1–2.5 times moles, to the starting material (Ia). Reaction temperature is −20°–150°C., particularly −5°–50° C. being preferable. Reaction period of time is 10 minutes to 72 hours, preferably 5–20 hours. Reaction pressure is 1–10 atmospheric pressure, preferably 1–3 atmospheric pressure. The free carboxylic acid is used at 0.8–4 times moles, preferably 1–3 times moles, to the starting material (Ia). After completion of the reaction, the desired product (Ib) is obtained by the same treatment as in Method A.

In Step [A-4], the desired compound (Ib) can be obtained by treatment of the compound (III) with a thiolcarboxylic acid or a salt thereof represented by the formula $$R^4CSM^1$$
$$\|$$
$$O$$

(wherein $R^4$ and $M^1$ are as defined above) in a suitable solvent or by treatment with the corresponding thiolcarboxylic acid in the presence of a base. As the solvent, there may be employed an alcohol such as methanol, ethanol, propanol, butanol and the like; an ether such as ether, tetrahydrofuran, dioxane and the like; an aromatic hydrocarbon such as benzene, toluene, xylene and the like; an alkyl halide such as chloroform, dichloromethane, trichlene and the like; an aprotic polar solvent such as dimethyl sulfoxide, phosphoric hexamethyltriamide, dimethylformamide and the like; and so on. As the base, there may be used an alkali metal hydroxide such as sodium hydroxide, potassium hydroxide, lithium hydroxide and the like; an alkali metal carbonate such as sodium carbonate, potassium carbonate, lithium carbonate, sodium hydrogencarbonate and the like; a tertiary amine such as triethylamine, trimethylamine, N,N-dimethylaniline, pyridine, lutidine and the like; and so on. Its amount to be used is 0.8–4 times moles, preferably 1–3 times moles, to thiolcarboxylic acid.

Also, the reaction may be rapidly completed under a mild condition by the addition of a catalyst. In this instance, if the reaction is carried out in a heterogeneous system by using an aromatic hydrocarbon such as benzene, toluene and the like or an ether such as ethyl ether or tetrahydrofuran as a solvent, isolation of the desired product (Ib) from water can be made more readily with simpler workup.

As the catalyst, there may be used a quaternary ammonium salt such as tetrabutylammonium bromide, tetrabutylammonium chloride, tetraethylammonium bromide, benzyltributylammonium bromide and the like and its amount to be used is 0.005–2 times moles, preferably 0.01–0.2 times mole, to the compound (III). Reaction temperature is −20°–150° C. and, in particular, preferably −5°–50° C. Reaction period of time is 10 minutes to 72 hours, preferably 1–24 hours. Reaction pressure is 1–10 atmospheric pressure, preferably 1–3 atmospheric pressure.

The thiolcarboxylic acid or salt thereof is used at 0.8–4 times moles, preferably 1–3 times moles, to the compound (III). After completion of the reaction, the reaction mixture is, if necessary, diluted with a solvent, washed with water and then the solvent is distilled off. Purification by a conventional method such as recrystallization or chromatography gives the compound (Ib).

In Step [A-5], the desired product (Ib) can be obtained by treatment of the compound (IV) with a thiolcarboxylic acid or a salt thereof represented by the formula $$R^4CSM^1$$
$$\|$$
$$O$$

(wherein $R^4$ and $M^1$ are as defined above) in a suitable solvent or by treatment with the corresponding free thiolcarboxylic acid in the presence of a base to effect a conjugate addition reaction. As the solvent, there may be used an alcohol such as methanol, ethanol, propanol, butanol and the like; an ether such as ether, tetrahydrofuran, dioxane and the like; an aromatic hydrocarbon such as benzene, toluene, xylene and the like; an alkyl halide such as chloroform, dichloromethane, Tri-Clene and the like; an aprotic polar solvent such as dimethylsulfoxide, hexamethylphosphoramide, dimethylformamide and the like; and so on. As the base, there may be used an alkali metal salt of an aliphatic carboxylic acid or carbonic acid such as sodium acetate, potassium acetate, sodium carbonate, potassium hydrogencarbonate and the like; a tertiary amine such as triethylamine, diethylamine, pyridine and the like; and so on. Its amount to be used is 0.005–4 times moles, preferably 0.01–2 times moles, to the starting material (IV). Reaction temperature is -20°–150° C., preferably -5°–50° C. Reaction period of time is 10 minutes to 72 hours, preferably 1–24 hours. Reaction pressure is 1–10 atmospheric pressure, preferably 1–3 atmospheric pressure.

The thiolcarboxylic acid or salt thereof may be used at 0.8–4 times moles, preferably 1–3 times moles, to the compound (IV). After completion of the reaction, the reaction mixture is treated in the same manner as in Step [A-4] to give the desired compound (Ib).

In Step [A-6], the desired product (Ic) can be obtained by treatment of the compound (II) with a mercaptan or a salt thereof represented by the formula $$R^6-SM^1$$

(wherein $R^6$ and $M^1$ are as defined above) in the presence of a dehydrogenation agent and a deoxidation agent in a suitable solvent. As the solvent, there may be used an ether such as diethyl ether, tetrahydrofuran, dioxane and the like; an alkyl halide such as chloroform, dichloromethane, Tri-Clene and the like; an aromatic hydrocarbon such as benzene, toluene, xylene and the like; and so on. As the dehydrogenation agent, there may be used a diester of an azocarboxylic acid such as diethyl azodicarboxylate, diisopropyl azodicarboxylate and the like. Its amount to be used is 0.8–4 times moles, preferably 1–2 times moles, to the starting material (II). As the deoxidation agent, there may be used a phosphine such as triphenyl phosphine, tri-n-butylphosphine, triethyl phosphine and the like. Its amount to be used is 0.8–4 times moles, preferably 1–3 times moles, to the starting material (II). Reaction temperature is −20°–150° C., in particular, −5–50° C. being preferable. Reaction period of time is 10 minutes to 72 hours, preferably 1–24 hours. Reaction pressure is 1–10 atmospheric pressures, preferably 1–3 atmospheric pressure.

The mercaptan or salt thereof is used at 0.8–4 times moles, preferably 1–3 times moles, to the starting material (II). After completion of the reaction, the reaction mixture is, if necessary, diluted with a usual solvent, washed with water and then the solvent is distilled off. Purification by the conventional methods such as recrystallization or chromatogrpahy gives the compound (Ic).

In Step [A-7], the desired product (Ic) can be prepared by treating the compound (Ia) with an alkylating agent represented by the formula $$R^6-X^1$$

(wherein $R^6$ is as defined above and $X^1$ represents a halogen atom such as chlorine, bromine or iodine atom or a sulfonic acid ester residue such as a methanesufonyloxy group, a p-toluenesufonyloxy group and the like) in the presence of a base in a suitable solvent. As the solvent, there may be used an aromatic hydrocarbon such as toluene, benzene, xylene and the like; an ether such as ethylether, tetrahydrofuran, dioxane and the like; an alkyl halide such as chloroform, dichloromethane, Tri-Clene and the like; an alcohol such as metanol, ethanol, n-propanol and the like; and so on. As the base, there may be used as alkali metal hydroxide such as sodium hydroxide, potassium hydroxide, lithium hydroxide, and the like; an alkali metal carbonate such as potassium carbonate, sodium carbonate, sodium hydrogencarbonate and the like; an alkali metal salt of an aliphatic carboxylic acid such as sodium acetate, potassium propionate and the like; a tertiary amine such as triethylamine, dimethylaniline, pyridine, lutidine and the like; and so on. Its amount to be used is 0.8–4 times moles, preferably 1–3 times moles, to the starting material (Ia). Reaction temperature is $-20°-150°$ C., in particular, $-5°-50°$ C. being preferable. Reaction period of time is 10 minutes to 72 hours, preferably 1–24 hours. Reaction pressure is 1–10 atmospheric pressure, preferably 1–3 atmospheric pressure.

The alkylating agent is used at 0.8–4 times moles, preferably 1–3 times moles, to the starting material (Ia).

After completion of the reaction, the reaction mixture is, if necessary, diluted with a usual extract solvent, washed with water and then the solvent is distilled off. Purification by a conventional method such as recrystallization or chromatography gives the compound (Ic).

In Step [A-8], the desired product (Ic) can be obtained by treatment of the compound (III) with a mercaptan or a salt thereof represented by the formula $$R^6-SM^1$$

(wherein $R^6$ and $M^1$ are as defined above) in a suitable solvent or by treatment with the corresponding mercaptan in the presence of a base to effect a sulfidation reaction. As the solvent, there may be used the same as in Step [A-2]. As the base, there may be used the same as in Step [A-4]. The amount thereof to be used is 0.8–4 times moles, preferably 1–2 times moles, to the starting material (III). Reaction temperature is $-20°-150°$ C., preferably $-5°-50°$ C. Reaction period of time is 10 minutes to 72 hours, preferably 1–24 hours. Reaction pressure is 1–10 atmospheric pressure, preferably 1–3 atmospheric pressure.

The mercaptan or salt thereof is used at 0.8–4 times moles, preferably 1–3 times moles, to the starting material (III). After completion of the reaction, the reaction mixture is, if necessary, diluted with a solvent, washed with water and then the solvent is distilled off. Purification by the conventional methods such as recrystallization or chromatography gives the desired product (Ic). In Step [A-9], the desired product (Ic) can be obtained by treatment of the compound (IV) with a mercaptan or a salt thereof represented by the formula $$R^6-SM^1$$

(wherein $R^6$ and $M^1$ are as defined above) in a suitable solvent or by treatment with the corresponding mercaptan in the presence of a base to effect a conjugate addition reaction. As the solvent, there may be used an aromatic hydrocarbon such as toluene, benzene, xylene and the like; an ether such as ethyl ether, tetrahydrofuran, dioxane and the like; an alcohol such as methanol, ethanol, n-propanol, t-butanol and the like; an alkyl halide such as chloroform, dichloromethane, Tri-Clene and the like; an aprotic polar solvent such as dimethyl sulfoxide, phosphoric hexamethyltriamide, dimethylformamide and the like; and so on. As the base, there may be used a tertiary amine such as triethylamine, trimethylamine, pyridine, lutidine, N,N-diemthylaniline and the like; an alkali metal hydroxide such as sodium hydroxide, potassium hydroxide, lithium hydroxide and the like; an alkali metal carbonate such as sodium carbonate, potassium carbonate, sodium hydrogencarbonate and the like. The amount thereof to be used 0.005–4 times moles, preferably 0.01–2 times moles, to the starting material (IV). Reaction temperature is $-20°-150°$ C., preferably $-10-50°$ C. Reaction period of time is 15 minutes to 72 hours, preferably 30 minutes to 24 hours. Reaction pressure is 1–10 atmospheric pressure, preferably 1–3 atmospheric pressure. The mercaptan or salt htereof is used at 0.8–4 times moles, preferably 1–3 times moles, to the compound (IV). After completion of the reaction, the reaction mixture is, if necessary, diluted with a solvent, washed with water and then the solvent is distilled off. Purification by a conventional method such as recrystallization or chromatography gives the compound (Ic).

In each of the above-mentioned Synthetic routes, where the end product contains a reactive substituent such as, for example, an amino group, said substituent may be previously protected with a suitable protecting group, if necessary, and after the reaction may be completed, the protecting group may be removed to give the desired product.

For instance, where the compound having the following formula (Ib-1) is to be prepared, a compound (Ia-1) is subjected to reaction with a p-aminobenzoic acid derivative having the amino group protected with a carbobenzyloxy group and then said protecting group can be removed to give the desired product.

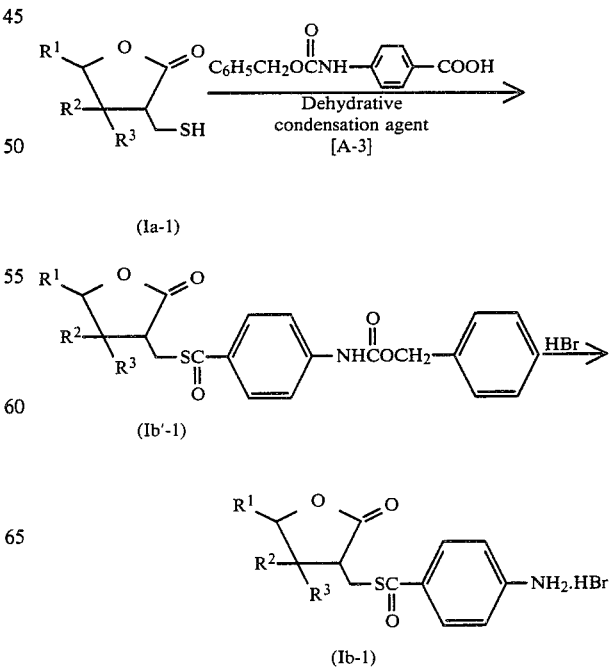

The above compounds (II)–(IV) which may be employed as starting materials in this invention may be prepared according to the following steps by the procedures as disclosed in literatures.

acetic acid and sodium acetate to effect elimination reaction, according to the procedures as disclosed in J. Am. Chem. Soc., 80, 3079 (1958), (Step [c]).

For preparing the present compound having a substi-

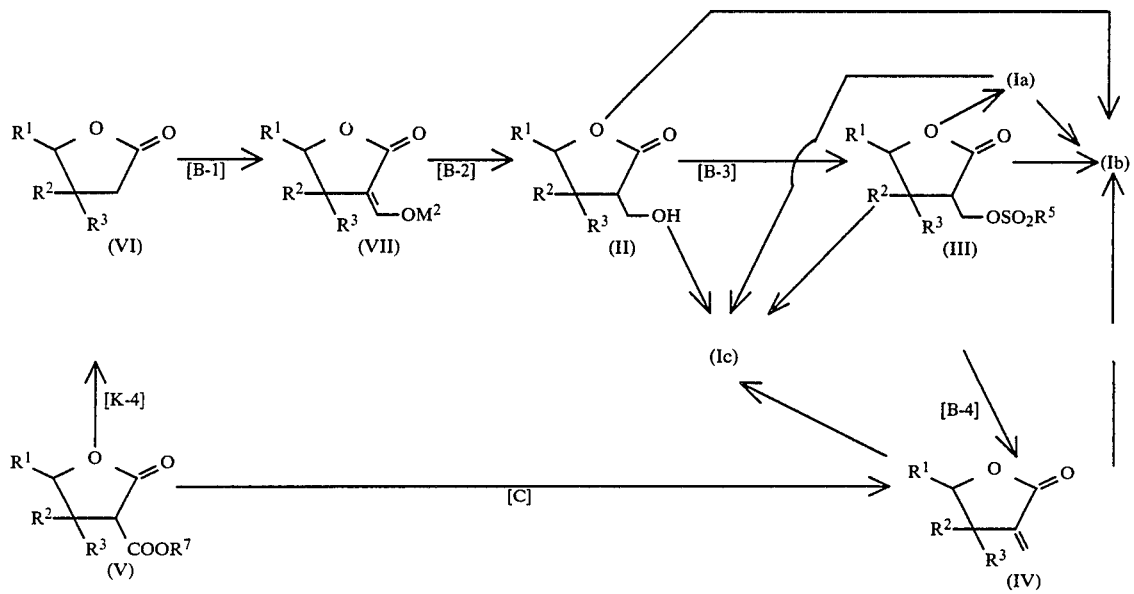

In the preparation steps, $R^1$, $R^2$, $R^3$, $R^5$ and $M^1$ are as defined above and $R^7$ represents a straight or branched alkyl group having 1–5 carbon atoms.

Following the procedures as described in Tetrahedron Letters, 1293 (1973), the compound (VII) is obtained by treatment of the compound (VI) with ethyl formate in the presence of a strong base such as sodium hydride and the like to effect a formylation reaction (Step [B-1]).

The compound (VII) is reduced by a hydride, for example, with sodium borohydride in acetic acid or is catalytically hydrogenated with Raney Nickel and the like, according to the procedures as described in J. Chem. Soc. (c), 1967, 1575, to yield the compound (II) (Step [B-2]).

This compound (II) is treated with a compound represented by the formula $R^5SO_2Cl$ (wherein $R^5$ is as defined above) to give the compound (III), according to the procedures as disclosed in Reagents for Organic Synthesis, Vol. 1, 662 (Step [B-3]).

The compound (IV) can be obtained by treating this compound (III) for elimination reaction with an organic base such as diazabicycloundecene (DBU), diazabicyclononene (DBN), pyridine and the like, according to the procedures as described in J. Chem. Soc. (c), 1967, 1575, (Step [B-4]). Also, the compound (IV) may be prepared by hydrolysis of the ester (V) to the free carboxylic acid, treatment with diethylamine and formalin to form a Mannich base, and subsequent treatment with tuted phenyl group, the compound (III) having an unsubstituted phenyl group is first prepared and then a substituent may be introduced as required; alternatively, a series of steps may be carried out under the form wherein a substituted phenyl group is originally introduced or said group is protected with a suitable protecting group and then, if necessary, replacement of a substituent may be effected or a protecting group may be removed.

For preparing the compound having a nitro-substituted phenyl group, the compound (III) in the form of an unsubstituted phenyl group is prepared and then preferably subjected to nitration. The introduced nitro group may also be converted to an amino or cyano group, if necessary.

For preparing the compound wherein a phenyl group is substituted with an alkyl group, a carboxy group or an alkoxycarbonyl group, the compound (III) having a halogenated phenyl group is first prepared and then a halogen atom is preferably converted to an alkyl group, a carboxy group or an alkoxycarbonyl group.

γ-Butyrolactone (VI) is an important intermediate for the synthesis of the present compound (I). Studies on synthesis of γ-butyrolactone have been earnestly made in recent years and they are summarized as the reviews, for example, in Synthesis, 1975, 67; Heterocycles, 14, 661 (1980); Journal of Synthetic Organic Chemistry. Japan, 39, 358 (1981) and so on. Some of them are shown below.

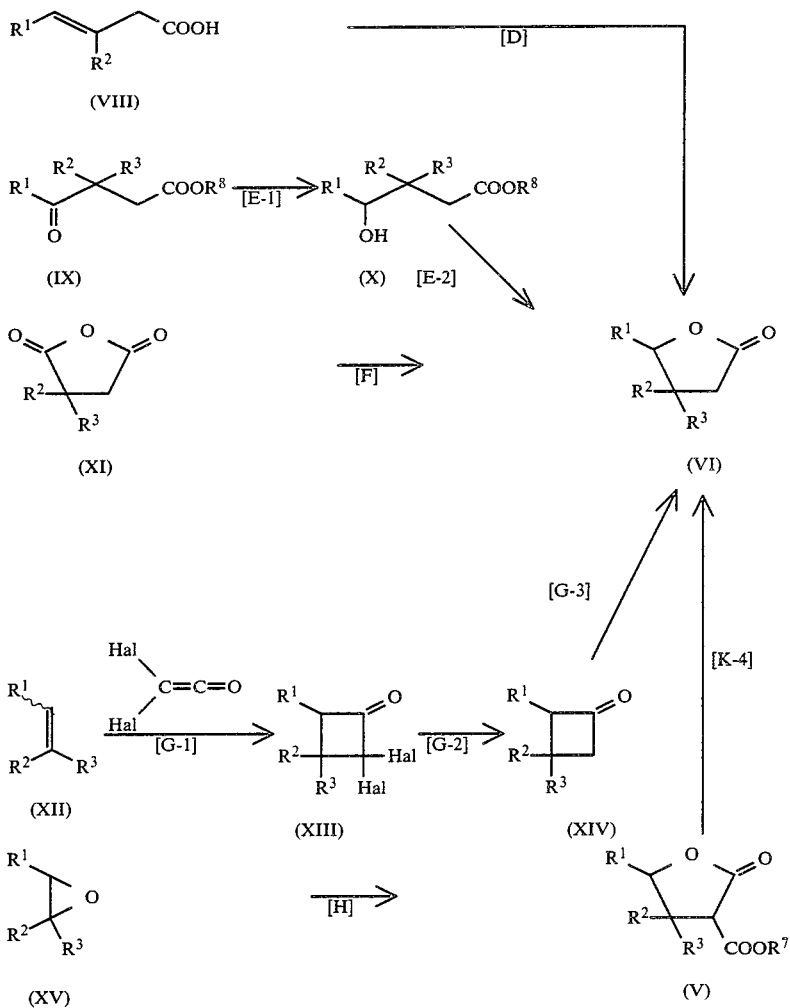

In the above steps, $R^1$, $R^2$, $R^3$, $R^7$ and Hal are as defined above.

There is a method for direct ring closure of a β,γ-unsaturated carboxylic acid (VIII) in the presence of an acid catalyst (Step [D]); a method wherein a γ-ketocarboxylic acid (IX) as a starting material is converted to a γ-hydroxycarboxylic acid (X) by reduction of a carbonyl group and then cyclized by heating (Steps [E-1]–[E-2]); a method wherein a carbonyl group of succinic anhydride (XI) is reduced (Step [F]); a method wherein an olefin (XII) and a dihalogenoketene are subjected to cycloaddition reaction to form an α,α-dihalogenocyclobutanone (XIII) (Step [G-1]), a halogen atom is replaced by a hydrogen atom by reduction (Step [G-2]), and then Baeyer-Villiger oxidation reaction is effected to form a γ-butyrolactone (VI); a method wherein an epoxide (XV) is subjected to reaction with a malonic acid diester in the presence of a base to form an α-alkoxycarbonyl-Y-butyrolactone (V) (Step [H]) followed by hydrolysis and decarbonation and so on. However, these reactions are not always satisfactory in view of easy availability of a starting material, yield, easiness in reaction, position specificity of substituents in the desired Y-butyrolactone (VI) and others.

The present inventors have, therefore, made studies to improve the preparation of a γ-butyrolactone (VI) and, as a result, developed a novel process for preparing a Y-butyrolactone (VI') which comprises a series of steps as illustrated below.

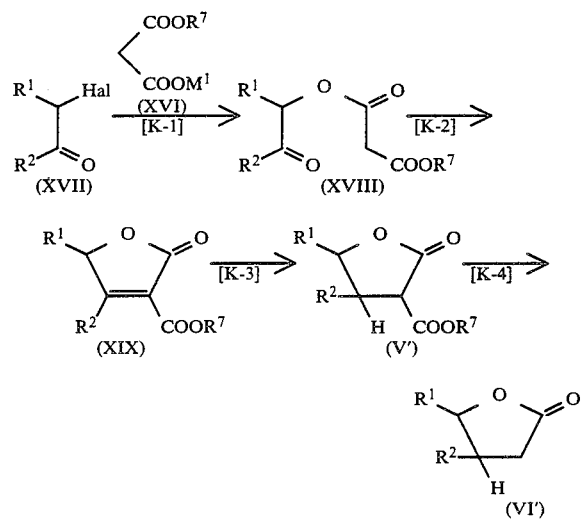

In the above steps, $R^1$, $R^2$, $R^7$, Hal and $M^1$ are as defined above.

This process can meet the above-mentioned requirements and has, in particular, the advantage that a series of reactions (Steps [K-1]-[K-4]) can be carried out in the single reaction vessel and there is no need to isolate and purify each intermediate during the reactions. Namely, a γ-butyrolactone (VI') can be synthesized directly from a starting α-halogenoketone (XVII). If necessary, the intermediates may be of course isolated and purified during each step and the reactions may be effected stepwisely.

A process for preparing the intermediate (VI') will be explained in detail hereinbelow.

Step [K-1]

An α-halogenoketone (XVII) is treated with a salt of a malonic acid monoester (XVI) in a suitable solvent to form a malonic acid keto ester (XVIII). As the starting α-halogenoketone (XVII), there may be employed any commercially available ones. If not easily available, it may be synthesized by any suitable process, for example, that of Organic Synthesis Coll., Vol. 2, 480. A salt of a malonic acid monoester (XVI) may be commercially available, but it may be readily synthesized from a malonic acid diester accoridng to the process described in Organic Synthesis Coll., Vol. 4, 417 (1963). As the solvent, there may be used an aromatic hydrocarbon such as toluene, benzene, xylene and the like; an alkyl halide such as chloroform, dichloromethane, Tri-Clene and the like; an ether such as ethyl ether, tetrahydrofuran, dioxane and the like; an aprotic polar solvent such as dimethylformamide, dimethyl sulfoxide, hexamethylphosphoramide, acetonitrile and the like and the amount thereof to be used is preferably of a weight ratio of 1-200 times to the compound (XVII). Reaction temperature is −50°-150° C. and, in particular, preferably −5°-50° C. Reaction period of time is 1 minute to 24 hours, preferably 30 minutes to 10 hours.

After completion of the reaction, subsequent Step [K-2] may be usually followed directly, but, where the intermediate (XVIII) is to be isolated, extraction is done with a conventional solvent such as ether, toluene and the like and then it may be isolated and purified by a conventional method, e.g., recrystallization, distillation or chromatography.

Step [K-2]

Following the proceeding Step [K-1], the compound (XVIII) is cyclized with dehydration by treating with a catalyst to form an α-alkoxycarbonyl-α,β-unsaturated γ-butyrolactone (XIX).

As the catalyst, there may be used, for example, an ammonium salt of an aliphatic carboxylic acid such as ammonium acetate, ammonium formate and the like or an aliphatic carboxylic acid salt of a strongly basic ion exchange resin. The amount thereof to be used is 0.01-2 times moles, preferably 0.1-1.0 times moles, to the compound (XVII). Reaction temperature is −20°-150° C., in particular, preferably −5°-50° C. Reaction period of time is 5 minutes to 24 hours, preferably 15 minutes to 10 hours. Reaction pressure is 1-10 atmospheric pressure, preferably 1-3 atmospheric pressure.

When the reaction is conducted continuously from Step [K-1], it is not necessary to add a solvent newly. However, where the intermediate (XVIII) is to be isolated, there may be employed the same solvent as in Step [K-1].

After completion of the reaction, subsequent Step [K-3] is usually followed directly, but, if necessary, the intermediate (XIX) may be isolated in a conventional manner, e.g., extraction, distillation, recrystallization, chromatography and so on.

Step [K-3]

An α-alkoxycarbonyl saturated γ-butyrolactone (V') can be obtained by carrying out the chemical reduction process in which the intermediate (XIX) is treated with a reducing agent or the hydrogenation reaction (catalytic hydrogenation) of the double bond with a hydrogen gas in the presence of a catalyst.

In the chemical reduction process, there may be employed as a reducing agent, for example, a borohydride such as sodium borohydride, sodium cyanoborohydride, zinc borohydride, lithium borohydride and the like. The amount thereof to be used is 0.8-10 times moles, preferably 1-3 times moles, to the compound (XVII). In order to make Step [K-3] progress smoothly, it is preferred to add an acid. As the acid which may be employed in the Step, there may be mentioned, for example, an aliphatic carboxylic acid such as acetic acid, propionic acid and the like; a mineral acid such as hydrochloric acid, sulfuric acid and the like; gaseous carbonic acid or dry ice, a protonic acid, e.g., a weakly acidic ion exchange resin and the like. In this instance, the amount of the acid to be used is 0.1-20 times moles, preferably 0.3-5 times moles, to the compound (XVII). In addition to the aforesaid protonic acid, there may also be employed a Lewis acid. As the Lewis acid, there may be mentioned, for example a transition metal chloride such as nickel chloride, palladium chloride, rhodium chloride and the like. The amount thereof to be used is 0.01-2.0 times moles, preferably 0.05-1.0 times moles, to the compound (XVII). Reaction temperature is −20°-150° C., preferably −5°-50° C. Reaction period of time is 5 minutes to 48 hours, preferably 30 minutes to 10 hours. Where this Step [K-3] is to be conducted directly from Step [K-2], it is not necessary to add a solvent newly.. However, where the intermediate (XIX) is to be isolated, there may be employed the same solvent as in Step [K-2].

After completion of the reaction, subsequent Step [K-4] may be usually followed directly, but the intermediate (V') may be, if necessary, isolated in a conventional manner, e.g., extraction, distillation, recrystallization, chromatography and the like.

In the catalytic reduction process, there may be employed as the catalyst, for example, palladium-carbon, platinum-carbon, rhodium-carbon, palladium-barium sulfate and the like and the amount thereof to be used is of a weight ratio of 0.1-100%, preferably 1-20%, to the compound (XVII). Reaction temperature is −20°-150° C., preferably 0°-100° C. Reaction period of time is 15 minutes to 48 hours, preferably 30 minutes to 24 hours. Reaction pressure is 1-200 atmospheric pressure, preferably 1-100 atmospheric pressure.

When this Step [K-4] is to be conducted continuously from Step [K-3], it is not necessary to add a solvent newly, but acetic acid or ethanol may be further added, if necessary. Where the intermediate (XIX) is to be isolated, it is preferred to use the following solvent, namely, an alcohol such as methanol, ethanol, propanol and the like; an aliphatic carboxylic acid such as acetic acid, propionic acid and the like; an ether such as ethyl ether, tetrahydrofuran, dioxane, dimethoxyethane and the like; an aromatic hydrocarbon such as benzene, toluene, xylene and the like. Where a solvent other than a carboxylic acid is used and a reaction is slow, it is preferable to add a small amount of acetic acid, hydrochloric acid, perchloric acid or the like.

Usually, after completion of the reaction, the catalyst is filtered off and the filtrate is removed to subsequent Step [K-4]. Where the intermediate (V') is to be isolated, usual treatment, e.g., extraction, distillation, recrystallization, chromatography and the like is effected.

Step [K-4]

The intermediate (V') is subjected to decarboxylation by heating in water and a suitable organic solvent to yield the important intermediate, γ-butyrolactone (VI').

Where this Step [K-4] is conducted continuously from Step [K-3], water solely is added and then decarboxylation is done with heating. When a boiling point of the solvent employed in Step [K-3] is not higher than 100° C., it is preferable to once distill off the solvent under reduced pressure, replace with a high-boiling solvent and then conducting the reaction. Where the intermediate (V') is to be isolated, decarboxylation is carried out by heating in water and a suitable solvent.

Reaction temperature is 0°–300° C., preferably 60°–200° C. Reaction period of time is 30 minutes to 48 hours, preferably 1–10 hours.

Where this Step [K-4] is effected continuously from Step [K-3], it is not necessary to add an organic solvent newly. Where the intermediate (V') is isolated and where one replace with a high-boiling solvent, there may be preferably employed, for example, an aromatic hydrocarbon such as toluene, xylene and the like; an aprotic polar solvent such as hexamethylphosphoramide, dimethylformamide, dimethyl sulfoxide and the like; an aliphatic carboxylic acid such as acetic acid, propionic acid and the like.

After completion of the reaction, direct distillation is done or the reaction mixture is poured into a large volume of water, the precipitate thus separated is recovered by filtration and purified by distillation or recrystallization; alternatively, the reaction mixture is extracted with an ordinary solvent and then isolated and purified by distillation or recrystallization to afford γ-butyrolactone (VI').

The present compound (I) has characteristics of a remarkable immunomodulating activity and further of an extremely low toxicity, as compared with known immunoregulatory agents.

More specifically, the present compounds were tested for an antibody formation potentiating activity in mice and an adjuvant arthritis inhibiting activity in rats and, as a result, potent antibody formation potentiating activity and adjuvant authritis inhibiting activity were observed. Moreover, the present compounds showed $LD_{50}$ of 2,000 mg/kg or more and thus they have been confirmed to have an extremely low toxicity.

From the foregoing, the present compound can be widely applied as immunomodulating preparations to treatment of autoimmune diseases such as rheumatoid arthritis, nephritis, systemic lupus erythematosus and the like as well as diseases caused by immunoinsufficiency such as malignant tumor, serious infection and the like.

The immunomodulating composition according to this invention may contain as an active ingredient a compound of the above formula (I) or a pharmaceutically acceptable salt or cyclodextrin inclusion compounds thereof together with a solid or liquid pharmaceutical additives such as diluents, stabilizers and the like. Where the compound (I) is acidic, a particularly preferable salt thereof may include a pharmaceutically acceptable non-toxic salt such as an alkali metal salt or an alkaline earth metal salt; for example, there may be mentioned a sodium, potassium, magnesium or calcium salt or an aluminium salt. There may be also mentioned preferably such suitable amine salts as an ammonium salt, a lower alkyl amine(e.g., triethylamine)salt, a hydroxy-lower alkyl amine[e.g., 2-hydroxyethylamine, bis-(2-hydroxyethyl)amine or tri-(2-hydroxyethyl)amine] salt, a cycloalkyl amine(e.g., dicyclohexyl amine)salt, a benzylamine (e.g., N,N-dibenzylethylenediamine)salt and a dibenzyl amine salt. Where the compound (I) is basic, a particularly preferable salt thereof may include such non-toxic salts as hydrochloride, methanesulfonate, hydrobromide, sulfate, phosphate, fumarate, succinate and the like. These salts are most preferable for injection in view of solubility in water. The compound represented by general formula (I) may be converted into a cyclodextrin inclusion compound according to an ordinary method such as the saturated aqueous solution method, the kneading ? method, the lyophilizing method and so on, using $\alpha$-, $\beta$-, or $\gamma$-cyclodextrin or a mixture thereof, thereby to improve the solubility and the bioavailability of the compound (I). In the immunomodulating composition, a ratio of the therapeutically effective ingredient to the carrier may be varied from 1% by weight to 90% by weight. The present immunomodulating composition may be orally administered in the dosage form of granules, fine granules, powders, tablets, hard capsules, soft capsules, syrups, emulsions, suspensions or solutions or intravenously, intramuscularly or subcutaneously administered in the dosage form of injections. Also, it may be applied for an external use in the dosage form of suppositories, ointments or plasters. For preparing the present immunomodulating composition, there may be employed any pharmaceutical organic or inorganic, solid or liquid additives suitable for oral, rectal, parenteral or topical administration. As the diluents which may be employed for preparing solid preparations, there may be used, for example, lactose, sucrose, starch, talc, cellulose, dextrin, kaolin, calcium carbonate and the like. Liquid preparations for oral administration, e.g., emulsions, syrups, suspensions, solutions and the like may contain any inert diluent commonly employable, for example, water or a vegetable oil. Such preparations may also contain auxillary agents, e.g., moistening agents, suspending agents, sweetening agents, aromatic substances, coloring agents, preservatives and the like. Liquid preparations may be incorporated into a capsule, e.g., gelatin. As solvents or emulsifying agents which may be employed for preparing parenteral preparations, e.g., injections, suppositories, ointments and the like, there may be mentioned, for example, propylene glycol, polyethylene glycol, benzyl alcohol, ethyl oleate and the like. As the base for suppositories, there may be mentioned, for example, cacao butter, emulsified cacao butter, laurin, Witepsol and the like. These preparations may be prepared in conventional manner.

Clinical dosage, when orally administered, is generally a daily dose for adults of 0.1–1000 mg, preferably 1–300 mg, of the present compound, but it may be more preferable to optionally increase and decrease said dose, depending upon age, symptom, severity and so on. The aforesaid daily dose of the immunomodulating preparations may be administered once per day, in two or three divided forms at suitable intervals daily or intermittently.

When the present composition is to be applied as injections, it is preferable to continuously or intermittently administer a single dose of 0.05–300 mg of the present compound.

The following examples, experiments and preparations are offered by way of illustration and not by way of limitation.

PREPARATION 1

Synthesis of β-(p-chlorophenyl)-γ-butyrolactone (VI′)

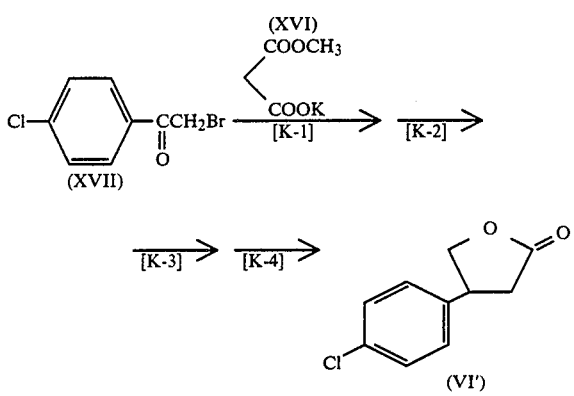

PREPARATION 2

Synthesis of various β-aryl-γ-butyrolactones VI′)

To 204 ml of dimethyl sulfoxide were added 40.1 g of potassium salt of monomethyl malonate (XVI) and then 50.0 g of p-chlorophenacyl bromide (XVII), and the mixture was stirred at room temperature for 30 minutes. Then, 12.9 g of ammonium acetate were added and the mixture was stirred at room temperature for 2 hours. Subsequently, 36.6 ml of acetic acid were added and 8.5 g of sodium borohydride were added under ice-cooling over one hour. The reaction mixture was allowed to stand at room temperature for one hour to reduce the double bond. After 68 ml of ice-water were added, the mixture was heated under reflex at 125°–130° C. for 3 hours to effect decarboxylation. After completion of the reaction, the reaction mixture was poured into 500 ml of ice-water, the black precipitate thus separated was collected by filtration and subjected to distillation under reduced pressure to give 29.7 g of the title compound (yield 71%).

m.p. 52°–54° C.

b.p. 150°–155° C./0.5 mmHg

IR spectrum $\nu_{max}^{KBr}$ cm$^{-1}$: 1770, 1490, 1425, 1155, 1020

NMR spectrum δ(CCl$_4$): 7.1 (s,4H), 3.4–3.7 (m, 3H), 2.5–2.7 (dd,2H)

Following the same procedures as in Preparation 1, there were prepared various β-aryl-γ-butyrolactones (VI′) as shown in the following Table 1.

TABLE 1

| R² | Yield (%) | Physical property |
|---|---|---|
| 2-chlorophenyl | 52 | IR $\nu_{max}^{CCl_4}$ cm$^{-1}$: 1780, 1475, 1440, 1160, 1025<br>NMR δ(CCl$_4$): 7.2(s, 4H), 3.6~4.8(m, 3H), 2.6~2.8 (s, 2H) |
| phenyl | 64 | IR $\nu_{max}^{CCl_4}$ cm$^{-1}$: 1790, 1165, 1025, 695<br>NMR δ(CCl$_4$): 7.2(s, 5H), 3.5~4.7(m, 3H), 2.5~2.8 (dd, 2H) |
| 4-methylphenyl | 71 | IR $\nu_{max}^{CCl_4}$ cm$^{-1}$: 1780, 1155, 1020<br>NMR δ(CCl$_4$): 7.0(s, 4H), 3.3~4.6(m, 3H), 2.5~2.7 (dd, 2H), 2.3(s, 3H) |
| 3-methylphenyl | 60 | IR $\nu_{max}^{CCl_4}$ cm$^{-1}$: 1780, 1610, 1490, 1165, 1030, 700<br>NMR δ(CCl$_4$): 6.3~6.8(m, 4H), 3.5~4.8(m, 3H), 2.5~2.8(dd, 2H), 2.3(s, 3H) |
| 2-methylphenyl | 60 | IR $\nu_{max}^{CCl_4}$ cm$^{-1}$: 1770, 1450, 1150, 1015<br>NMR δ(CCl$_4$): 7.0(s, 4H), 3.6~4.6(m, 3H), 2.4~2.7 (dd, 2H), 2.3(s, 3H) |

TABLE 1-continued

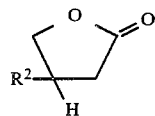

| R² | Yield (%) | Physical property |
|---|---|---|
| 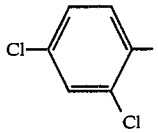 | 45 | IR $\nu_{max}^{KBr}$ cm⁻¹: 1770, 1475, 1165, 1010<br>NMR δ(CCL₄): 7.4(s, 1H), 7.3(s, 2H), 3.9~4.7(m, 3H), 2.6~2.9(t, 2H) |
| 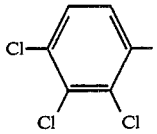 | 51 | IR $\nu_{max}^{CCl4}$ cm⁻¹: 1780, 1445, 1170, 1050, 1020<br>NMR δ(CDCl₃): 7.0~7.5(q, 2H), 4.0~4.8(m, 3H), 2.5~2.9(m, 2H), 2.6(s, 3H) |
| 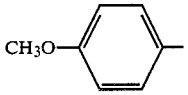 | 56 | IR $\nu_{max}^{KBr}$ cm⁻¹: 1760, 1240, 1220, 1160, 1010<br>NMR δ(CCl₄): 6.6~7.1(q, 4H), 3.4-4.6(m, 3H), 3.7(s, 3H), 2.5~2.7(m, 2H) |
| 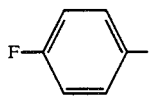 | 41 | IR $\nu_{max}^{KBr}$ cm⁻¹: 1760, 1220, 1160, 1010<br>NMR δ(CDCl₃): 6.8~7.3(m, 4H), 3.5~4.8(m, 3H), 3.6~3.9(dd, 2H). |

PREPARATION 3

Synthesis of sodium salt of β-(p-chlorophenyl)-β-formyl-γ-butyrolactone (VII)

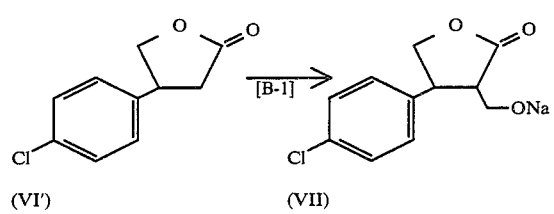

(VI')  (VII)

To a suspension of 9.1 g of 50% sodium hydride in 120 ml of anhydrous toluene was added dropwise a solution of 29.7 g of β-(p-chlorophenyl)-γ-butyrolactone (VI') obtained in Preparation 1 and 45 ml of ethyl formate in 84 ml of toluene over 10 minutes, while an inner temperature was maintained at 15°-20° C., and the mixture was then stirred at room temperature for 40 minutes. After completion of the reaction, excess sodium hydride was decomposed with methanol and the reaction mixture was filtered to give 37.0 g of the title compound as a pale brown solid (quantitative yield).

m.p. 170° C. (decomp.)

IR spectrum $\nu_{max}^{KBr}$ cm⁻¹: 1715, 1530, 1345, 1070

PREPARATION 4

Synthesis of β-(p-chlorophenyl)-α-hydroxymethyl-γ-butyrolactone (II)

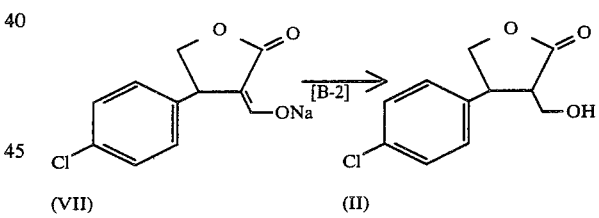

(VII)  (II)

To a mixture of 22.0 g of sodium salt of β-(p-chlorophenyl)-α-formyl-γ-butyrolactone (VII) obtained in Preparation 3 and 161 ml of acetic acid were added 4.56 g of sodium borohydride over one hour, while an inner temperature was maintained at 10°-20° C. The reaction was effected under ice-cooling for 30 minutes and at room temperature for one hour. Then, 20 ml of methanol was added to the reaction mixture, the solvent was distilled off under reduced pressure and the residue was added to 500 ml of an ice-water containing 50 g of potassium carbonate to saparate a white precipitate. It was collected by filtration, dried and then recrystallized from a mixed solvent of ethyl acetate and ethyl ether to give 11.9 g (yield, 65%) of the title compound as a colorless prism. The steric relationship between the hydroxymethyl group and the p-chlorophenyl group in the compound was found to be a trans configuration.

m.p. 95°-96° C.

IR spectrum $\nu_{max}^{KBr}$ cm⁻¹: 1760, 1495, 1175, 1020

PREPARATION 5

Synthesis of β-(p-chlorophenyl)-α-methanesulfonyloxymethyl-γ-butyrolactone (III)

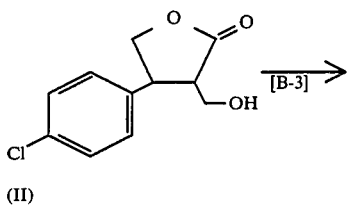

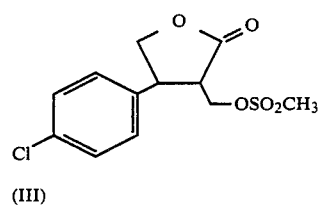

To a mixture of 2.4 g of β-(p-chlorophenyl)-α-hydroxymethyl-γ-butyrolactone (XII) and 1.1 ml of methanesulfonyl chloride in 17 ml of dichloromethane were added under ice-cooling 1.2 ml of pyridine. The mixture was stirred under ice-cooling for 3.5 hours and at room temperature for 48 hours. After completion of the reaction, the reaction mixture was washed in a conventional manner with 10% hydrochloric acid, water, 10% aqueous potassium carbonate and then saturated saline, and the organic layer was dried over magnesium sulfate. After filtration, the filtrate was concentrated, an oily residue was crystallized from a mixed solvent of ethyl acetate and ethyl ether to give 2.73 g (yield, 85%) of the title compound as a colorless powder.

m.p. 64°–65° C.

IR spectrum $\nu_{max}^{KBr}$ cm$^{-1}$: 1780, 1495, 1350, 1175, 950

EXAMPLE 1

Synthesis of β-(p-chlorophenyl)-α-(p-methylbenzoylthiomethyl)-γ-butyrolactone (Compound No. 1) (Ib)

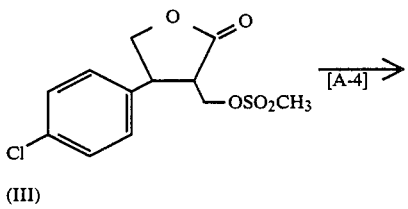

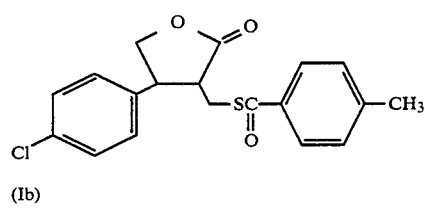

To a solution of 2.7 g of β-(p-chlorophenyl)-α-methanesulfonyloxymethyl-γ-butyrolactone (III) obtained in Preparation 4 in 35 ml of toluene were added 2.0 g of potassium p-methylthiolbenzoate and then 100 mg of tetra-n-butylammonium bromide. The mixture was stirred at room temperature for one hour. After completion of the reaction, the mixture was washed with water, dried over magnesium sulfate and the solvent was distilled off. The so-obtained crude product was recrystallized from ethyl ether to give 2.22 g (yield 68%) of the title compound as a white crystal.

m.p. 99°–100° C.

IR spectrum $\nu_{max}^{KBr}$ cm$^{-1}$: 1780, 1655, 1170, 1150 1010, 910

EXAMPLE 2

Synthesis of various α-acylthiomethyl-γ-butyrolactones (Ib)

Following the same procedures as in Example 1, there were obtained various α-acylthiomethyl-γ-butyrolactones (Ib) as shown with Compounds No. 2–63 in the following Table 2.

In the following Table, IR spectral data were measured in a KBr tablet unless otherwise indicated and expressed in cm$^{-1}$ unit. Also, NMR spectral data are δ values with ppm unit.

EXAMPLE 3

Synthesis of α-(p-n-butylbenzoylthiomethyl)-β-phenyl-γ-butyrolactone (Compound No. 64) (Ib)

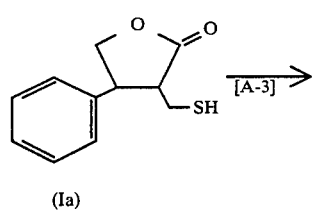

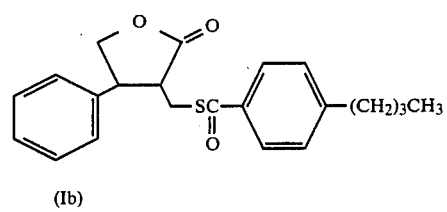

To a solution of 1.5 g of α-mercaptomethyl-β-phenyl-γ-butyrolactone in 30 ml of ethyl ether were added at room temperature 4.3 g of p-n-butylbenzoyl chloride and then 1.9 ml of pyridine. The mixture was kept at room temperature for 2.5 hours. After completion of the reaction, the reaction mixture was diluted with 100 ml of ethyl ether, washed with 10% hydrochloric acid, 10% aqueous sodium hydrogen carbonate and then satureated saline, dried over magnesium sulfate and the solvent was distilled off. The crude product thus obtained was purified by a silica gel column chromatography to give 2.1 g (yield 79%) of the title compound.

m.p. 91°–93° C.

IR spectrum $\nu_{max}^{KBr}$ cm$^{-1}$: 1765, 1660, 1210, 1170 1005, 905

EXAMPLE 4

Synthesis of various α-acylthiomethyl-β-phenyl-γ-butyrolactones (Ib)

Following the same procedures as in Example 3, there were obtained various α-acylthiomethyl-β-phe-

EXAMPLE 5

Synthesis of
α-benzoylthiomethyl-β-(p-chlorophenyl)-γ-butyrolactone (Compound No. 74) (Ib)

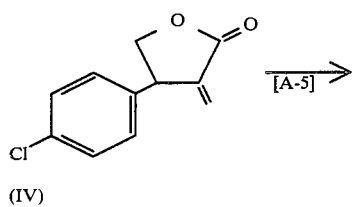

(IV)

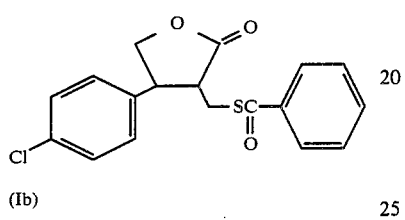

(Ib)

To a solution of 600 mg of β-(p-chlorophenyl)-α-methylene-γ-butyrolactone in 10 ml of toluene were added 0.44 ml of thiobenzoic acid and one drop of triethylamine and the reaction was effected at room temperature for 18 hours. The reaction mixture was diluted with 100 ml of ethyl ether, washed with water and saturated saline, dried over magnesium sulfate and the solvent was then distilled off. The crude product thus obtained was purified by a silica gel column chromatography to give 750 mg (yield 75%) of the title compound.
m.p. 99°–101° C.
IR spectrum $\nu_{max}^{CCl_4}$ cm$^{-1}$: 1780, 1660, 1195, 1175, 910

EXAMPLE 6

Synthesis of
α-acetylthiomethyl-β-(p-chlorophenyl)-γ-butyrolactone (Compound No. 75) (Ib)

Following the same procedures as in Example 5, there was obtained the title compound (Ib) as shown with Compound No. 75 in the following Table 2.

EXAMPLE 7

Synthesis of
α-(o-fluorobenzoylthiomethyl)-β-phenyl-γ-butyrolactone (Compound No. 76) (Ib)

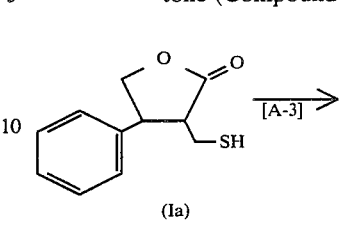

(Ia)

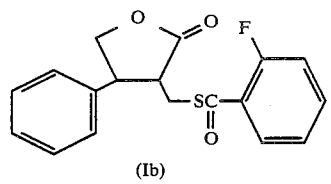

(Ib)

To a solution of 1.2 g of o-fluorobenzoic acid and 1.5 g of α-mercaptomethyl-β-phenyl-γ-butyrolactone in 20 ml of dimethylformamide were added 1.9 ml of diphenylphosphoryl azide (DPPA) and then 1.2 ml of triethylamine under ice-cooling. Then, the mixture was raised to a room temperature and stirred for 18 hours. After completion of the reaciton, the reaction mixture was diluted with 200 ml of ethyl ether, washed with 5% hydrochloric acid, saturated aqueous sodium hydrogencarbonate, and saturated saline, dried over magnesium sulfate and the solvent was then distilled off. The crude product thus obtained was purified by a silica gel column chromatography to give 1.6 g (yield 67%) of the title compound.
m.p. 92°–94° C.
IR spectrum $\nu_{max}^{KBr}$ cm$^{-1}$: 1765, 1645, 1270, 915, 760

EXAMPLE 8

Synthesis of various
α-acylthiomethyl-β-aryl-γ-butyrolactones (Ib)

Following the same procedures as in Example 7, there were obtained various α-acylthiomethyl-β-aryl-γ-butyrolactones (Ib) as shown with Compounds No. 77–78 in the following Table 2.

TABLE 2

(Ib)

| Compound No. | R$^1$ | R$^2$ | R$^4$ | Yield (%) | m.p. (°C.) | Physical property |
|---|---|---|---|---|---|---|
| 2 | H | phenyl | Cl-phenyl | 90 | 70~72 | IR: 1775, 1650, 1205, 910 |
| 3 | | | phenyl | 55 | 99~101 | IR: 1770, 1665, 1215, 910 |
| 4 | | | CH$_3$O-phenyl | 87 | — | IR(CCl$_4$): 1775, 1655, 1595, 905<br>NMR(CCl$_4$): 6.7~7.8(q,4H), 7.2(s,5H),<br>3.0~4.6(m,6H), 3.8(s,3H) |

TABLE 2-continued
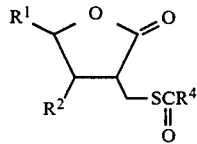
(Ib)
| Compound No. | R¹ | R² | R⁴ | Yield (%) | m.p. (°C.) | Physical property |
|---|---|---|---|---|---|---|
| 5 | | | NO₂—C₆H₄— | 61 | 91~93 | IR: 1780, 1660, 1360, 925 |
| 6 | | | F—C₆H₄— | 84 | 92~94 | IR: 1760, 1650, 1590, 1140, 915 |
| 7 | | | CH₃—C₆H₄— | 79 | 86~88 | IR: 1765, 1650, 1605, 915 |
| 8 | | | (CH₃)₂CHS—C₆H₄— | 21 | 63~65 | IR: 1780, 1670, 1590, 915 |
| 9 | | | 3-CH₃-C₆H₄— | 47 | 90~91 | IR: 1770, 1665, 1250, 1010 |
| 10 | | | 2-CH₃-C₆H₄— | 86 | 50~51 | IR: 1770, 1660, 1180, 895 |
| 11 | | | C₂H₅—C₆H₄— | 98 | 62~63 | IR: 1770, 1660, 1170, 910 |
| 12 | | | (CH₃)₃O—C₆H₄— | 88 | 64~65 | IR: 1775, 1660, 1025, 910 |
| 13 | CH₃—C₆H₄— | | C₆H₅— | 59 | 72~74 | IR: 1775, 1680, 1015, 910 |
| 14 | | | CH₃O—C₆H₄— | 93 | — | IR(CCl₄): 1780, 1660, 1605, 1030, 915<br>NMR(CCl₄): 6.6~7.9(q,4H), 7.0(s,4H), 2.8~4.6(m,6H), 3.7(s,3H), 2.2(s,3H) |
| 15 | | | 2-CH₃-C₆H₄— | 60 | 61~63 | IR: 1765, 1665, 1010, 900 |
| 16 | | | 3-CH₃-C₆H₄— | 87 | 113~115 | IR: 1770, 1680, 1020, 800 |
| 17 | | | CH₃—C₆H₄— | 71 | 84~86 | IR: 1765, 1650, 1015, 905 |
| 18 | | | F—C₆H₄— | 78 | 88~89 | IR: 1775, 1660, 1010, 915 |
| 19 | | Cl—C₆H₄— | 2-CH₃-C₆H₄— | 54 | 67~69 | IR: 1760, 1655, 1005, 900 |

TABLE 2-continued $$\text{(Ib)}$$

Structure: R¹-CH-O-C(=O) ring with R² and -CH-SCR⁴(=O) substituent

| Compound No. | R¹ | R² | R⁴ | Yield (%) | m.p. (°C.) | Physical property |
|---|---|---|---|---|---|---|
| 20 | | | 3-CH₃-C₆H₄- | 56 | 73~74 | IR: 1775, 1650, 1015, 820, 790 |
| 21 | | | 4-C₂H₅-C₆H₄- | 49 | 103~104 | IR: 1780, 1660, 1180, 1155, 915 |
| 22 | | | 4-(CH₃)₃O-C₆H₄- | 48 | 122~124 | IR: 1780, 1655, 1215, 1015, 910 |
| 23 | | 4-Cl-C₆H₄- | 4-F-C₆H₄- trans | 64 | 117~118 | IR: 1775, 1665, 1205, 1150, 1010, 910 |
| 24 | | | 4-F-C₆H₄- cis | 42 | 119~121 | IR: 1760, 1655, 1200, 1155, 910 |
| 25 | | 4-CH₃O-C₆H₄- | C₆H₅- | 29 | 84~86 | IR: 1775, 1655, 1030, 915 |
| 26 | | 4-NO₂-C₆H₄- | | 26 | 139~142 | IR: 1775, 1665, 1515, 1345, 905 |
| 27 | | 4-F-C₆H₄- | | 57 | 86~87 | IR: 1760, 1650, 1210, 1005, 910 |
| 28 | | 2-CH₃-C₆H₄- | 4-CH₃-C₆H₄- | 46 | 88~91 | IR: 1780, 1660, 1010, 910 |
| 29 | | | C₆H₅- | 57 | — | IR(CCl₄): 1785, 1675, 1025, 915, 690<br>NMR(CCl₄): 6.9~7.9(m,9H),<br>3.0~4.5(m,6H), 2.3(s,3H) |
| 30 | | | 3-CH₃-C₆H₄- | 79 | 83~85 | IR: 1770, 1660, 1140, 1010 |
| 31 | | | 2-CH₃-C₆H₄- | 42 | — | IR: 1780, 1670, 1145, 1025, 905<br>NMR(CCl₄): 7.0~7.5(m,8H),<br>3.1~4.6(m,6H), 2.3(s,3H),<br>2.4(s,3H) |
| 32 | | 3-CH₃-C₆H₄- | C₆H₅- | 70 | 83~84 | IR: 1770, 1660, 1005, 900 |
| 33 | | | 4-NO₂-C₆H₄- | 48 | 77~78 | IR: 1770, 1670, 1520, 1350, 1200, 1015 |
| 34 | | | 4-CH₃-C₆H₄- | 65 | 73~75 | IR: 1775, 1665, 1010, 910 |
| 35 | | 2-Cl-C₆H₄- | C₆H₅- | 50 | 79~80 | IR: 1780, 1670, 1020, 915 |

TABLE 2-continued $$\underset{R^2}{\overset{R^1}{\diagdown}}\overset{O}{\underset{}{\bigcirc}}\overset{O}{\underset{SCR^4}{\diagdown}}$$ (Ib)

| Compound No. | R¹ | R² | R⁴ | Yield (%) | m.p. (°C.) | Physical property |
|---|---|---|---|---|---|---|
| 36 | | | CH₃—⟨phenyl⟩— | 59 | 90~92 | IR: 1780, 1765, 1660, 1015, 910 |
| 37 | | | (CH₃)₂CHSO₂—⟨phenyl⟩— | 21 | — | IR(CCl₄): 1780, 1670, 1595, 1180, 915<br>NMR(CCl₄): 7.1~7.8(m,8H),<br>4.2~4.7(m,2H),<br>3.8~4.1(m,1H),<br>3.0~3.6(m,3H), 1.3(d,6H) |
| 38 | | NH₂—⟨phenyl⟩— | CH₃—⟨phenyl⟩— | 39 | — | IR(CCl₃): 1775, 1660, 1520, 1015, 910<br>NMR(CHCl₃): 7.1~7.8(q,4H),<br>6.5~7.1(q,4H),<br>3.0~4.7(m,8H), 2.4(s,3H) |
| 39 | | ⟨o-tolyl (CH₃)⟩— | F—⟨phenyl⟩— | 75 | — | IR(CCl₄): 1775, 1660, 1595, 1150, 1015, 910<br>NMR(CCl₄): 6.8~7.9(m,8H),<br>3.0~4.6(m,6H), 2.3(s,3H) |
| 40 | | ⟨phenyl⟩— | CH₃— | 79 | 54~55 | IR(CCl₄): 1780, 1695, 1130, 1020, 960 |
| 41 | | | CH₃(CH₂)₃— | 26 | — | IR(CCl₄): 1785, 1695, 1140, 1120, 1025<br>NMR(CCl₄): 7.2(s,5H),<br>3.8~4.6(m,2H),<br>2.8~3.6(m,4H), 2.4(t,2H),<br>0.8~1.8(b,7H) |
| 42 | | CH₃—⟨phenyl⟩— | CH₃— | 58 | 61~63 | IR: 1770, 1690, 1140, 1005<br>IR(CCl₄): 1775, 1690, 1140, 1020 |
| 43 | | CH₃(CH₂)₃— | | 44 | — | NMR(CCl₄): 7.1(s,4H),<br>3.5~4.6(m,2H),<br>2.6~3.4(m,4H),<br>1.9~2.6(m,2H), 2.3(s,3H),<br>0.6~1.8(m,7H) |
| 44 | | Cl—⟨phenyl⟩— | | 47 | — | IR(CCl₄): 1785, 1695, 1495, 1145, 1030<br>NMR(CCl₄): 7.2(s,4H),<br>3.9~4.6(m,2H),<br>2.8~3.6(m,4H),<br>2.3~2.7(m,2H),<br>0.8~1.8(m,7H) |
| 45 | | CH₃O—⟨phenyl⟩— | CH₃— | 40 | 76~79 | IR(CHCl₃): 1765, 1685, 1245, 1120, 1010 |
| 46 | | NO₂—⟨phenyl⟩— | | 59 | 98~99 | IR: 1785, 1705, 1515, 1345, 1015 |
| 47 | | F—⟨phenyl⟩— | | 64 | 53~55 | IR: 1765, 1695, 1220, 1130, 1015 |
| 48 | | ⟨o-tolyl (CH₃)⟩— | | 53 | 79~80 | IR(CCl₄): 1780, 1695, 1130, 1020 |
| 49 | | | CH₃(CH₂)₃— | 59 | — | IR(CCl₄): 1780, 1690, 1140, 1020<br>NMR(CCl₄): 7.0~7.3(m,4H),<br>3.6~4.6(m,3H),<br>3.0~3.3(m,3H), 2.3(s,3H),<br>2.2~2.5(m,2H), |

TABLE 2-continued (Ib) structure: R¹ and R² on a γ-butyrolactone ring with -CH₂-S(=O)-R⁴ substituent

| Compound No. | R¹ | R² | R⁴ | Yield (%) | m.p. (°C.) | Physical property |
|---|---|---|---|---|---|---|
| | | | | | | 0.8~1.7(b,7H) |
| 50 | | 3-CH₃-C₆H₄- | CH₃— | 57 | 36~37 | IR: 1770, 1680, 1135, 1015 |
| 51 | | 2-Cl-C₆H₄- | | 51 | 113~114 | IR: 1775, 1765, 1700, 1125, 1010 |
| 52 | CH₃(CH₂)₃— | H | | 22 | — | IR(CCl₄): 1780, 1700, 1180, 1130, 1005, 960<br>NMR(CCl₄): 4.0~4.5(m,1H),<br>2.6~3.3(m,3H), 2.3(s,3H),<br>1.8~2.2(m,2H),<br>0.8~1.8(m,9H) |
| 53 | | | C₆H₅- | 20 | — | IR(CCl₄): 1780, 1670, 1210, 1180, 1005, 915<br>NMR(CCl₄): 7.2~8.1(m,5H),<br>4.0~4.6(m,1H),<br>2.5~3.6(m,3H),<br>1.9~2.4(m,2H),<br>0.7~1.8(m,9H) |
| 54 | H | C₆H₅-CH₂- | CH₃— | 46 | 98-100 | IR: 1760, 1690, 1155, 1130, 1010 |
| 55 | | H | | 62 | — | IR (liquid film): 1770, 1690, 1155, 1135, 1020<br>NMR(CDCl₃): 3.9~4.5(m,2H),<br>2.5~3.4(m,4H),<br>1.8~2.5(m,1H), 2.3(s,3H) |
| 56 | | 4-CN-C₆H₄- | C₆H₅- | 79 | 129~131 | IR: 1775, 1660, 1145, 1000, 900 |
| 57 | | 2,4-Cl₂-C₆H₃- | | 63 | 76~78 | IR: 1780, 1645, 1210, 1020, 925, 905 |
| 58 | | 4-CH₃(CH₂)₄-C₆H₄- | | 76 | 54~55 | IR: 1790, 1655, 1205, 1145, 1025, 915 |
| 59 | | 2,3,4-Cl₃-C₆H₂- | | 67 | 130~132 | IR: 1775, 1640, 1205, 1175, 1010, 900 |
| 60 | | 4-C₂H₅OOC-C₆H₄- | | 22 | 90~92 | IR: 1770, 1710, 1660, 1105, 1015, 910 |
| 61 | | H | | 41 | 30~33 | IR: 1760, 1655, 1150, 1020, 910 |
| 62 | C₆H₅- | | CH₃— | 58 | 57~58 | IR(CCl₄): 1775, 1695, 1155, 1125, 935 |
| 63 | H | cyclohexyl- | | 71 | 54~56 | IR(CCl₄): 1770, 1690, 1445, 1355, 1130, 1020, 955 |

TABLE 2-continued (Ib) structure: R¹, R² on furanone ring with —SCR⁴ where C has =O

| Compound No. | R¹ | R² | R⁴ | Yield (%) | m.p. (°C.) | Physical property |
|---|---|---|---|---|---|---|
| 65 | | phenyl | 3,4,5-trimethoxyphenyl (CH₃O×3) | 86 | — | IR(CCl₄): 1780, 1660, 1325, 1130, 1000<br>NMR(CCl₄): 7.2(s,5H), 7.0(s,2H),<br>3.8(s,9H), 3.1~4.7(m,6H) |
| 66 | | | phenyl-CH₂— | 66 | — | IR(CCl₄): 1775, 1690, 1140, 1020<br>NMR(CCl₄): 7.2(s,10H), 3.7~4.6(m,3H),<br>3.6(s,2H), 2.8~3.3(m,3H) |
| 67 | | | C₂H₅— | 79 | 34~35 | IR(CCl₄): 1775, 1690, 1135, 1015 |
| 68 | | | NC-C₆H₄— | 88 | 132~133 | IR: 1760, 1600, 1205, 1010, 915 |
| 69 | | | 2-(COOCH₃)C₆H₄— | 32 | — | IR: 1780, 1730, 1680, 1280, 1140, 1020, 915<br>NMR(CCl₄): 7.2(s,5H), 7.1~7.8(m,4H),<br>3.8(s,3H), 2.9~4.7(m,6H) |
| 70 | | | CH₃(CH₂)₂— | 67 | — | IR(CCl₄): 1770, 1680, 1130, 1010<br>NMR(CCl₄): 7.2(s,5H), 3.8~4.6(m,2H),<br>2.7~3.6(m,4H), 2.4(t,2H),<br>1.2~1.9(m,2H), 0.9(t,3H) |
| 71 | | | (CH₃)₂CH— | 90 | 36~37 | IR(CCl₄): 1770, 1680, 1130, 1015, 965 |
| 72 | | | CH₃(CH₂)₄— | 69 | 37~39 | IR(CCl₄): 1770, 1690, 1400, 1015 |
| 73 | | | CH₃(CH₂)₆— | 100 | — | IR(CCl₄): 1785, 1710, 1145, 1025<br>NMR(CCl₄): 7.2(s,5H), 3.9~4.6(m,2H),<br>2.8~3.6(m,4H),<br>2.1~2.6(m,2H),<br>0.8~1.8(m,13H) |
| 75 | | 4-Cl-C₆H₄— | CH₃— | 56 | 69~71 | IR(CCl₄): 1775, 1685, 1125, 1020, 950 |
| 77 | | | 2-F-C₆H₄— | 49 | 57~58 | IR: 1770, 1670, 1015, 915 |
| 78 | | phenyl | 3,4-(CH₃)₂C₆H₃— | 53 | 74~75 | IR: 1775, 1660, 1015, 945 |

EXAMPLE 9

Synthesis of α-(p-aminobenzoylthiomethyl)-β-phenyl-γ-butyrolactone hydrobromide (Compound No. 79) (Ib)

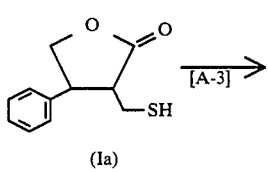
(Ia)

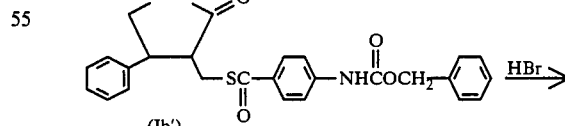
(Ib')

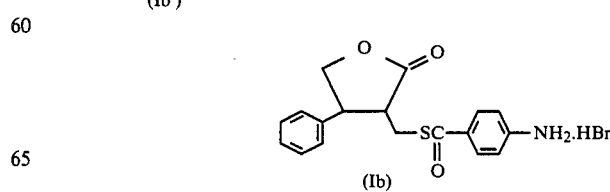
(Ib)

Following the same procedures as in Example 7, there were obtained 2.2 g (yield 50%; m.p. 160°–162° C.) of α-(p-carbobenzyloxyaminobenzoylthiomethyl)-β-phenyl-γ-butyrolactone from 2.0 g of α-mercaptomethyl-β-phenyl-γ-butyrolactone and 3.1 g of p-carbobenzyloxyaminobenzoic acid, using a condensing agent diphenylphosphoryl azide. Then, in order to remove the protective group, the so-obtained product was treated with 44 ml of a 30% hydrobromic acid solution in acetic acid at room temperature for one hour. To the reaction mixture were added 350 ml of ethyl ether and the crystalline substance thus formed was recovered by filtration and then dried to give 2.1 g (yield 100%) of the title compound.

m.p. 211°–213° C.

matography to give 400 mg (yield 52%) of the title compound.

m.p. 41°–42° C.

IR spectrum $\nu_{max}^{KBr}$ cm$^{-1}$: 1765, 1140, 990, 755, 695

EXAMPLE 11

Synthesis of β-(p-chlorophenyl)-α-mercaptomethyl-γ-butyrolactone (Compound No. 81)(Ia) and α-mercaptomethyl-γ-phenyl-γ-butyrolactone (Compound No. 82)(Ia)

Following the same procedures as in Example 10, there were obtained those compounds shown with Compounds No. 81 and No. 82 in the following Table 3.

TABLE 3

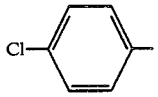

(Ia)

| Compound No. | R$^1$ | R$^2$ | Yield (%) | m.p. (°C.) | Physical property |
|---|---|---|---|---|---|
| 81 | H | Cl—C$_6$H$_4$— | 14 | 84~85 | IR(CCl$_4$): 1775, 1190, 1130, 1030<br>NMR(CCl$_4$): 7.2(s,4H), 3.5~4.8(m,3H),<br>2.2~3.3(m,3H), 1.4~1.7(dd,1H) |
| 82 | C$_6$H$_5$— | H | 36 | 145~147 | IR: 1775, 1170, 935, 750<br>NMR(DMSO-d$_6$): 7.4(s,5H), 5.2~5.6(m,1H),<br>2.4~3.5(m,5H), 1.4~2.0(m,1H) |

IR spectrum $\nu_{max}^{KBr}$ cm$^{-1}$: 1780, 1655, 1200, 1000, 910

EXAMPLE 10

Synthesis of α-mercaptomethyl-β-phenyl-γ-butyrolactone (Compound No. 80) (Ia)

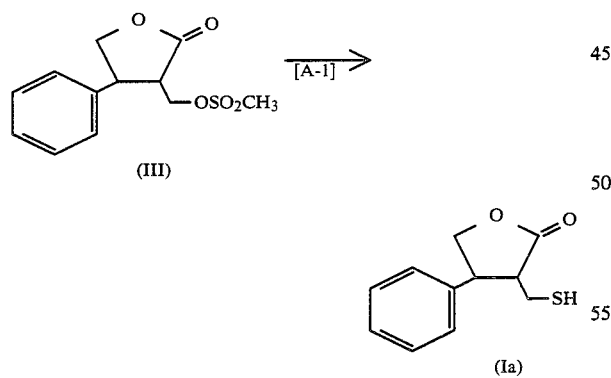

To a solution of 1.0 g of α-methanesulfonyloxymethyl-β-phenyl-γ-butyrolactone (III) in 20 ml of ethanol were added 1.5 ml of acetic acid and then 1.2 g of commercially available 70% sodium hydrosulfide and the mixture was stirred at room temperature for 18 hours. After completion of the reaction, the reaction mixture was diluted with 150 ml of ethyl acetate, washed with water in a conventional manner, dried over magnesium sulfate and the solvent was distilled off. The crude product thus obtained was purified by a column chro-

EXAMPLE 12

Synthesis of α-cyclohexylthiomethyl-β-(p-methoxyphenyl)-γ-butyrolactone (Compound No. 83)(Ic)

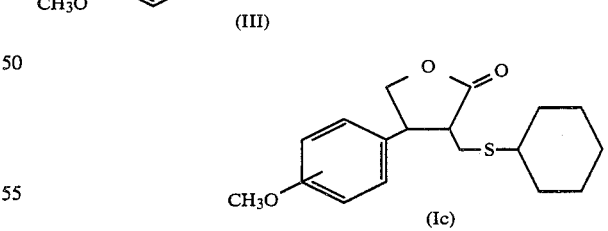

To a solution of 480 mg of potassium hydroxide in 40 ml of ethanol were added 2.0 g of α-methanesulfonyloxymethyl-β-(p-methoxyphenyl)-γ-butyrolactone and 1.6 ml of cyclohexylmercaptan and the resulting mixture was kept at room temperature for 4 hours. After completion of the reaction, the reaction mixture was diluted with 200 ml of ethyl ether, washed with water and saturated saline, dried over magnesium sulfate and the solvent was distilled off. The crude product thus obtained was purified by a silica gel column chromatography to give 600 mg (yield 22%) of the title compound.

m.p. 50°–51° C.
IR spectrum $\nu_{max}^{CCl_4}$ cm$^{-1}$: 1780, 1515, 1250, 1020

EXAMPLE 13

Synthesis of various β-aryl-γ-butyrolactone derivatives (Ic)

Following the same procedures as in Example 12, there were obtained those compounds shown with Compounds No. 84–93 in the following Table 4 and Compound No. 96 in the following Table 5.

EXAMPLE 14

Synthesis of α-benzylthiomethyl-β-(p-chlorophenyl)-γ-butyrolactone (Compound No. 94)(Ic)

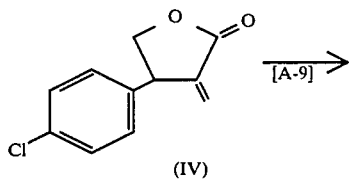

(IV) [A-9] →

TABLE 4

(Ic)

structure: R¹—CH(—O—C(=O)—)—CH(R²)—CH(—S—R⁶)

| Compound No. | R¹ | R² | R⁶ | Yield (%) | m.p. (°C.) | Physical property |
|---|---|---|---|---|---|---|
| 84 | H | phenyl | benzyl (–CH₂–C₆H₅) | 83 | 60~62 | IR(CCl₄): 1775, 1595, 1130, 1020 |
| 85 | | | CH₃(CH₂)₃— | 84 | — | IR(CCl₄): 1775, 1170, 1130, 1015  NMR(CCl₄): 7.2(s,5H), 3.4~4.7(m,3H), 2.2~3.1(m,5H), 0.6~1.7(m,7H) |
| 86 | | | CH₃— | 63 | — | IR(CCl₄): 1790, 1180, 1145, 1030  NMR(CCl₄): 7.2(s,5H), 3.5~4.7(m,3H), 2.7~3.1(m,3H), 2.0(s,3H) |
| 87 | | | cyclohexyl | 12 | 56~58 | IR(CCl₄): 1785, 1175, 1140, 1030 |
| 88 | | CH₃–C₆H₄– | –C₆H₄–CH₂– (benzyl) | 42 | 86~87 | IR: 1775, 1755, 1150, 1005, 815 |
| 89 | | | cyclohexyl | 27 | 38~40 | IR(CCl₄): 1780, 1120, 1020 |
| 90 | | CH₃O–C₆H₄– | –C₆H₄–CH₂– | 55 | 65~67 | IR: 1765, 1260, 1185, 1150, 1010 |
| 91 | | NO₂–C₆H₄– | cyclohexyl | 56 | — | IR(CHCl₃): 1775, 1520, 1350, 1025  NMR(CDCl₃): 7.2~8.3(q,4H), 3.5~4.9(m,3H), 2.2~3.2(m,4H), 0.9~2.1(m,10H) |
| 92 | | F–C₆H₄– | –C₆H₄–CH₂– | 32 | 59~60 | IR(CCl₄): 1770, 1230, 1140, 1020 |
| 93 | | | cyclohexyl | 61 | 62~64 | IR(CCl₄): 1770, 1225, 1010, 825 |

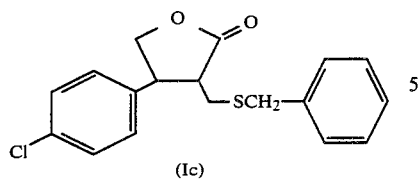

(Ic)

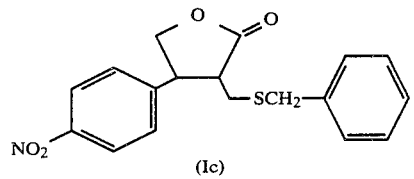

(Ic)

To a solution of 700 mg of β-(p-chlorophenyl)-α-methylene-γ-butyrolactone in 10 ml of toluene were added 0.51 ml of benzylmercaptan and one drop of triethylamine and the resulting mixture was kept at room temperature for 6 hours. After completion of the reaction, the reaction mixture was diluted with 100 ml of ethyl ether, washed with 10% aqueous sodium hydroxide and saturated saline, dried over magnesium sulfate and the solvent was distilled off. The crude product thus obtained was purified by a column chromatography to give 900 mg (yield 81%) of the title compound.

m.p. 66°–69° C.

IR spectrum $\nu_{max}^{CCl_4}$ cm$^{-1}$: 1775, 1490, 1180, 1020

EXAMPLE 15

Synthesis of α-benzylthiomethyl-β-(p-nitrophenyl)-γ-butyrolactone (Compound No. 95) (Ic)

To a solution of 71 mg of potassium hydroxide in 6 ml of ethanol were added 253 mg of α-mercaptomethyl-β-(p-nitrophenyl)-γ-butyrolactone and 239 mg of benzyl bromide and the resulting mixture was kept at room temperature for 4 hours. After completion of the reaction, the reaction mixture was diluted with 60 ml of ethyl acetate, washed with water and saturated saline, dried over magnesium sulfate and the solvent was distilled off. The resulting crude product was purified by a silica gel column chromatography to give 218 mg (yield 50%) of the title compound.

m.p. 90°–91° C.

IR spectrum $\nu_{max}^{KBr}$ cm$^{-1}$: 1755, 1345, 1140, 1010, 840

EXAMPLE 16

Synthesis of various spiro derivatives (Ib)

Following the same procedures as in Example 1, there were obtained those compounds shown with Compounds No. 97–99 in the following Table 5.

TABLE 5

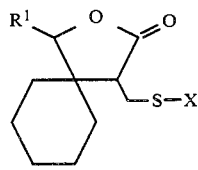

| Compound No. | R¹ | X | Yield (%) | m.p. (°C.) | Physical property |
|---|---|---|---|---|---|
| 96 | H | ⌬-CH₂— | 82 | — | IR(CCl₄): 1780, 1145, 1025, 700<br>NMR(CCl₄): 7.2(s,5H), 3.5~4.2(q,2H), 3.7(s,2H), 2.2~2.9(m,3H), 0.8~2.0(m,10H) |
| 97 | | CH₃CO— | 36 | 88~90 | IR(CHCl₃): 1770, 1690, 1135, 1015 |
| 98 | | ⌬-CO— | 65 | 74~76 | IR(CCl₄): 1780, 1660, 1205, 1140, 1015, 910 |
| 99 | | CH₃O-⌬-CO— | 46 | 87~89 | IR: 1760, 1640, 1580, 1150, 995, 905 |

EXAMPLE 17

Immunomodulating activity (1) Antibody Formation Potentiating Activity

ICR strain male mice of 5-weeks old (Shizuoka Farm), each group consisting of 5 mice, were employed for studying antibody formation potentiating activity of the present compound. Animals were sensitized by intraperitoneal injection of 200 μl of a 10% saline suspension of sheep red blood cell (Denka Seiken). After 4

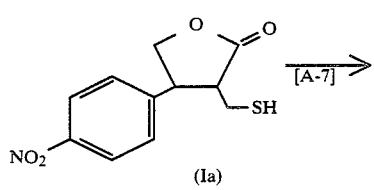

(Ia) [A-7]→ days, spleen was excised and Plaque Formation Cell (PFC) number was calculated according to the method by Cunningham et al [Cunningham, A.T. et al., Immunilogy, 14, 599(1968)]. The test compound was suspended in a 1% tragacanth solution and administered orally after the following day of sensitization at a volume of 10 ml/kg. Oral administration with solely a 1% tragacanth solution was applied for control.

Effect of the test compound is expressed in terms of $$\text{Stimulation Index } (S.I.) = \frac{PFC \text{ (medicated groups)}}{PFC \text{ (control groups)}}$$

The results are shown in Table 6.

TABLE 6

| Compound No. | S.I. | Compound No. | S.I. | Compound No. | S.I. |
|---|---|---|---|---|---|
| 1 | 1.85 | 28 | 2.08 | 66 | 1.87 |
| 3 | 1.65 | 30 | 2.69 | 67 | 1.94 |
| 4 | 1.79 | 31 | 3.08 | 70 | 2.72 |
| 5 | 2.73 | 34 | 1.49 | 71 | 1.92 |
| 6 | 1.81 | 39 | 1.76 | 72 | 1.77 |
| 7 | 2.75 | 40 | 1.56 | 73 | 1.76 |
| 10 | 2.20 | 41 | 3.34 | 74 | 2.23 |
| 11 | 1.71 | 43 | 1.47 | 76 | 1.64 |
| 12 | 1.41 | 44 | 1.69 | 78 | 1.47 |
| 13 | 1.92 | 48 | 1.91 | 81 | 1.54 |
| 14 | 2.55 | 49 | 3.07 | 84 | 1.94 |
| 16 | 1.47 | 50 | 1.50 | 86 | 1.59 |
| 20 | 2.15 | 56 | 1.62 | 87 | 2.06 |
| 21 | 1.73 | 61 | 1.41 | 88 | 1.50 |
| 23 | 1.98 | 62 | 2.76 | Control | 1.00 |
| 26 | 1.49 | 63 | 1.81 | | |

It will be apparent from the Table 6 that all present compounds exert a remarkable antibody formation potentiating activity.

(2) Adjuvant Arthritis Inhibiting Activity

F-344 strain male rats of 9 weeks old (Nippon Charles River), each group consisting of 8-10 rats, were employed for assessment of adjuvant arthritis inhibiting activity of the present compounds Arthritis was induced by subsutaneous injection of 100 μl of a 6% paraffin oil suspension of *Mycobacterium butyricum* into hind paw. The test compound was suspended in a 1% tragacanth solution and then administered orally everyday from the day of adjuvant injection up to the 21st day at a volume of 5 ml/kg. After 24 days from the sensitization, paw volume was measured Oral administration of solely a 1% tragacanth solution was applied for control. Paw volumes of adjuvant injected paws are shown in Table 7.

TABLE 7

| Compound No. | Dose (mg/Kg) | Paw volume (ml) |
|---|---|---|
| 23 | 3 | 2.84 ± 0.25* |
| | 30 | 2.78 ± 0.23* |
| | 300 | 3.03 ± 0.25 |
| | Control | 3.48 ± 0.11 |
| 40 | 30 | 3.18 ± 0.17* |
| | 300 | 3.18 ± 0.18* |
| | Control | 3.62 ± 0.06 |
| 83 | 30 | 3.00 ± 0.16* |
| | Control | 3.58 ± 0.20 |

*level of significance p < 0.05 (T-test)

It will be apparent from the Table 7 that all present compounds exert a significant adjuvant arthritis inhibiting activity.

EXAMPLE 18

Preparation of Tablets

Ten grams of finely divided α-acetylthiomethyl-β-phenyl-γ-butyrolactone (Compound No. 40), 89 g of lactose, 40 g of crystalline cellulose, 20 g of calcium carboxymethyl cellulose and 1 g of magnesium stearate were thoroughly admixed and the mixture was made into plain tablets, each containing 160 mg of the said compound, by direct compression. Such plain tablets were sugar-coated or film-coated to form sugar-coated or film-coated tablets.

EXAMPLE 19

Preparation of Capsules

Ten grams of finely divided α-acetylthiomethyl-β-phenyl-γ-butyrolactone (Compound No. 40), 89 g of corn starch, 70 g of lactose, 10 g of crystalline cellulose and 1.0 g of magnesium stearate were admixed and the mixture was made to capsules, each containing 180 mg of the said compound.

EXPERIMENT

Acute Toxicity Test

Using ddY strain male mice of 7-8 weeks old, each group consisting of 5 mice, a suspension of the present compound in a 1% tragacanth solution was administered orally. Then, mortality was examined by 3-days observation. The results are shown in Table 8.

TABLE 8

| Compound No. | Acute toxicity values (LD$_{50}$ mg/Kg) |
|---|---|
| 1 | >4,000 |
| 7 | >4,000 |
| 23 | >4,000 |
| 40 | >2,000 |
| 74 | >4,000 |
| 84 | >4,000 |
| Levamisole | <1,000 |

We claim:

1. A γ-butyrolactone derivative represented by the following formula:

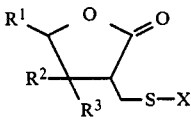

wherein R$^1$ represents a hydrogen atom, a straight or branched alkyl group having 1-8 carbon atoms, a phenyl group; R$^2$ and R$^3$ may be the same or different and each represents a hydrogen atom, a straight or branched alkyl group having 1-8 carbon atoms, a cycloalkyl group having 3-10 carbon atoms, a benzyl group, a phenyl group, a phenyl group substituted with a substituent selected from the group consisting of a halogen atom, an alkoxy group having 1-5 carbon atoms, a nitro group, an amino group, an alkyl group having 1-4 carbon atoms, a nitrile group and an alkoxycarbonyl group having 2-6 carbon atoms; R$^2$ and R$^3$ may be linked to form an alkylene group having 4-6 carbon atoms; X represents a hydrogen atom, a straight or branched alkyl group having 1-8 carbon atoms, a cycloalkyl group having 3-10 carbon atoms, a benzyl group or a substituent represented by the formula

wherein R⁴ represents a straight or branched alkyl group having 1-8 carbon atoms, a cycloalkyl group having 3-10 carbon atoms, a benzyl group, a phenyl group or a phenyl group substituted with a substituent selected from the group consisting of a halogen atom, an alkoxy group having 1-5 carbon atoms, a nitro group, an alkylthio group having 1-5 carbon atoms, a nitrile group, an alkoxycarbonyl group having 2-6 carbon atoms and an alkyl group having 1-4 carbon atoms or a salt thereof.

2. The γ-butyrolactone derivative according to claim 1, wherein, R¹ is a hydrogen atom, a straight alkyl group having 1-4 carbon atoms or a phenyl group, one of R² and R³ is a hydrogen atom and the other is a hydrogen atom, a substituted or unsubstituted phenyl group, a benzyl group or a cyclohexyl group or both are jointed to form an alkylene group having 4 or 5 carbon atoms, X is a hydrogen atom, a straight alkyl group having 1-4 carbon atoms, a cyclohexyl group, a benzyl group, a benzylcarbonyl group, a straight or branched alkanoyl group having 2-9 carbon atoms or a substituted or unsubstituted benzoyl group.

3. The γ-butyrolactone derivative according to claim 2, wherein, R¹ is a hydrogen atom or a phenyl group, one of R² and R³ is a hydrogen atom and the other is a hydrogen atom, a substituted or unsubstituted phenyl group or cyclohexyl group, X is a hydrogen atom, a straight alkyl group having 1-4 carbon atoms, a cyclohexyl group, a benzyl group, a benzylcarbonyl group, a straight or branched alkanoyl group having 2-7 carbon atoms or a substituted or unsubstituted benzoyl group.

4. The γ-butyrolactone derivative according to claim 3, wherein, R¹ is a hydrogen atom, one of R² and R³ is a hydrogen atom and the other is a substituted or unsubstituted phenyl group, X is a straight or branched alkanoyl group having 2-7 carbon atoms of a substituted of unsubstituted benzoyl group.

5. An immunomodulating composition which comprises a pharmaceutically acceptable carrier and as an active ingredient an immunomodulating effective amount of a γ-butyrolactone derivative represented by the formula

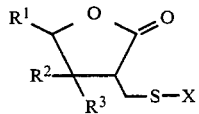

wherein R¹ represents a hydrogen atom, a straight or branched alkyl group having 1-8 carbon atoms, a phenyl group; R² and R³ may be the same or different and each represents a hydrogen atom, a straight or branched alkyl group having 1-8 carbon atoms, a cycloalkyl group having 3-10 carbon atoms, a benzyl group, a phenyl group, a phenyl group substituted with a substituent selected from the group consisting of a halogen atom, an alkoxy group having 1-5 carbon atoms, a nitro group, an amino group, an alkyl group having 1-4 carbon atoms, a nitrile group and an alkoxycarbonyl group having 2-6 carbon atoms; R² and R³ may be linked to form an alkylene group having 4-6 carbon atoms; X represents a hydrogen atom, a straight or branched alkyl group having 1-8 carbon atoms, a cycloalkyl group having 3-10 carbon atoms, a benzyl group or a substituent represented by the formula

wherein R⁴ represents a straight or branched alkyl group having 1-8 carbon atoms, a cycloalkyl group having 3-10 carbon atoms, a benzyl group, a phenyl group or a phenyl group substituted with a substituent selected from the group consisting of a halogen atom, an alkoxy group having 1-5 carbon atoms, a nitro group, an alkylthio group having 1-5 carbon atoms, a nitrile group, an alkoxycarbonyl group having 2-6 carbon atoms and an alkyl group having 1-4 carbon atoms or a salt thereof.

6. The immunomodulating composition according to claim 5, wherein, R¹ is a hydrogen atom, a straight alkyl group having 1-4 carbon atoms or a phenyl group, one of R² and R³ is a hydrogen atom and the other is a hydrogen atom, a substituted or unsubstituted phenyl group, a benzyl group or a cyclohexyl group or both are jointed to form an alkylene group having 4 or 5 carbon atoms, X is a hydrogen atom, a straight alkyl group having 1-4 carbon atoms, a cyclohexyl group, a benzyl group, a benzylcarbonyl group, a straight or branched alkanoyl group having 2-9 carbon atoms or a substituted or unsubstituted benzoyl group.

7. The immunomodulating composition according to claim 6, wherein, R¹ is a hydrogen atom or a phenyl group, one of R² and R³ is a hydrogen atom and the other is a hydrogen atom, a substituted or unsubstituted phenyl group or cyclohexyl group, X is a hydrogen atom, a straight alkyl group having 1-4 carbon atoms, a cyclohexyl group, a benzyl group, a benzylcarbonyl group, a straight or branched alkanoyl group having 2-7 carbon atoms or a substituted or unsubstituted benzoyl group.

8. The immunomodulating composition according to claim 7, wherein, R¹ is a hydrogen atom, one of R² and R³ is a hydrogen atom and the other is a substituted or unsubstituted phenyl group, X is a straight or branched alkanoyl group having 2-7 carbon atoms or a substituted or unsubstituted benzoyl group.

* * * * *